US008912367B2

(12) United States Patent
Hassan et al.

(10) Patent No.: US 8,912,367 B2
(45) Date of Patent: Dec. 16, 2014

(54) METHOD AND SYSTEM FOR LIQUID PHASE REACTIONS USING HIGH SHEAR

(75) Inventors: Abbas Hassan, Sugar Land, TX (US); Aziz Hassan, Houston, TX (US); Rayford G. Anthony, College Station, TX (US); Gregory Borsinger, Chatham, NJ (US)

(73) Assignee: H R D Corporation, Houston, TX (US)

( * ) Notice: Subject to any disclaimer, the term of this patent is extended or adjusted under 35 U.S.C. 154(b) by 272 days.

(21) Appl. No.: 13/530,032

(22) Filed: Jun. 21, 2012

(65) Prior Publication Data

US 2013/0345472 A1    Dec. 26, 2013

(51) Int. Cl.
| | |
|---|---|
| C07B 41/08 | (2006.01) |
| B01J 19/00 | (2006.01) |
| C07B 41/02 | (2006.01) |
| C07C 2/88 | (2006.01) |
| B01J 19/18 | (2006.01) |
| B01F 7/00 | (2006.01) |
| B01F 13/10 | (2006.01) |

(52) U.S. Cl.
CPC ............. *C07B 41/08* (2013.01); *B01J 19/0066* (2013.01); *C07B 41/02* (2013.01); *C07C 2/88* (2013.01); *B01J 19/1806* (2013.01); *B01F 7/00766* (2013.01); *B01F 13/1016* (2013.01); *B01J 2219/00083* (2013.01)
USPC ........... 568/884; 585/469; 585/638; 585/733; 568/579; 568/840

(58) Field of Classification Search
USPC ................... 585/469, 638, 733; 568/579–699, 568/840–923
See application file for complete search history.

(56) References Cited

U.S. PATENT DOCUMENTS

| | | | |
|---|---|---|---|
| 3,887,167 | A | 6/1975 | Irwin |
| 3,996,012 | A | 12/1976 | Zucker |
| 4,931,225 | A | 6/1990 | Cheng |
| 5,538,191 | A | 7/1996 | Holl |
| 5,597,044 | A | 1/1997 | Roberts et al. |
| 5,844,005 | A | 12/1998 | Bauman et al. |
| 5,877,350 | A | 3/1999 | Langer et al. |
| 6,096,789 | A | 8/2000 | Cleric et al. |
| 6,147,126 | A | 11/2000 | DeGeorge et al. |

(Continued)

FOREIGN PATENT DOCUMENTS

| | | |
|---|---|---|
| DE | 4235558 | 5/1994 |
| FR | 2825996 A1 | 12/2002 |
| JP | 2005319452 A | 11/2005 |
| WO | 02064708 A2 | 8/2002 |

OTHER PUBLICATIONS

"Caviation: A technology on the horizon," Current Science 91 (No. 1): 35-46 (2006).
IKA-Rotor-Stator Generators—2003 Processing Catalog (38 pgs.).

(Continued)

*Primary Examiner* — Brian McCaig
(74) *Attorney, Agent, or Firm* — Timothy S. Westby; Porter Hedges, LLP

(57) ABSTRACT

A method of reacting one or more components in a liquid phase to form an organic product, the method including feeding a carbon-based gas to a high shear device; feeding a hydrogen-based liquid medium to the high shear device; using the high shear device to form a dispersion comprising the carbon-based gas and the hydrogen-based liquid medium, wherein the dispersion comprises gas bubbles with a mean diameter of less than about 5 μm; introducing the dispersion into a reactor; and reacting the dispersion to produce the organic product.

20 Claims, 2 Drawing Sheets

(56) References Cited

U.S. PATENT DOCUMENTS

| | | |
|---|---|---|
| 6,193,504 B1 | 2/2001 | Chen et al. |
| 6,262,131 B1 | 7/2001 | Arcuri et al. |
| 6,368,366 B1 | 4/2002 | Langer et al. |
| 6,368,367 B1 | 4/2002 | Langer et al. |
| 6,383,237 B1 | 5/2002 | Langer et al. |
| 6,530,964 B2 | 3/2003 | Langer et al. |
| 6,742,774 B2 | 6/2004 | Holl |
| 6,822,007 B2 | 11/2004 | Ketley et al. |
| 6,924,316 B2 | 8/2005 | Iwamoto et al. |
| 7,005,541 B2 | 2/2006 | Cheung et al. |
| 7,608,744 B1 | 10/2009 | Johnston et al. |
| 7,863,489 B2 | 1/2011 | Johnston et al. |
| 2002/0089074 A1 | 7/2002 | Holl |
| 2003/0010013 A1 | 1/2003 | Johnstone |
| 2003/0043690 A1 | 3/2003 | Holl |
| 2004/0052158 A1 | 3/2004 | Holl |
| 2004/0157941 A1 | 8/2004 | Font Freide et al. |
| 2005/0033069 A1 | 2/2005 | Holl et al. |
| 2006/0245991 A1 | 11/2006 | Holl et al. |
| 2007/0186472 A1 | 8/2007 | Rabovitser et al. |
| 2009/0001316 A1 | 1/2009 | Hassan et al. |
| 2009/0003126 A1 | 1/2009 | Hassan et al. |
| 2009/0075364 A1 | 3/2009 | Fabiyi et al. |
| 2009/0205488 A1 | 8/2009 | Betting et al. |
| 2010/0217039 A1 | 8/2010 | Hassan et al. |
| 2010/0317748 A1 | 12/2010 | Hassan et al. |
| 2010/0329944 A1 | 12/2010 | Hassan et al. |
| 2011/0004033 A1 | 1/2011 | Johnston et al. |

OTHER PUBLICATIONS

Bibliographa Data and English Abstract of Publicatin No. DE4235558 dated May 11, 1994 (2 pgs.).

Bibliographa Data and English Abstract of Publication No. FR2825996 dated Dec. 20, 2002 (2 pgs.).

Bibliographa Data and English Abstract of Publication No. JP2005319452 dated Nov. 17, 2005 (2 pgs.).

Chattopadhyay et al., "Understanding Mechanical Energy Driven Nonequilibrium Processing: Some Results, Eleventh International Conference on Rapidly Quenched and Metastable Materials," A Material Science and Engineering, vol. 375-377, dated Jul. 15, 2004, pp. 72-77 (9 pgs).

Office Action dated Jun. 3, 2011 for U.S. Appl. No. 12/568,280 (16 pgs.).

Office Action dated Jun. 2, 2011 for U.S. Appl. No. 12/427,286 (12 pgs.).

Office Action dated Jun. 25, 2009 for U.S. Appl. No. 12/142,447 (10 pgs.).

Office Action dated Jan. 7, 2010 for U.S. Appl. No. 12/142,447 (6 pgs.).

Office Action dated May 13, 2010 for U.S. Appl. No. 12/142,447 (5 pgs.).

Office Action dated Feb. 4, 2010 for U.S. Appl. No. 12/492,721 (5 pgs.).

Office Action dated Feb. 18, 2010 for U.S. Appl. No. 12/635,433 (6 pgs.).

Office Action dated Feb. 18, 2010 for U.S. Appl. No. 12/635,454 (6 pgs.).

Office Action dated May 14, 2010 for U.S. Appl. No. 12/137,441 (15 pgs.).

Office Action dated Feb. 19, 2010 for U.S. Appl. No. 12/144,459 (10 pgs.).

Office Action dated Sep. 2, 2009 for U.S. Appl. No. 12/142,433 (11 pgs.).

Office Action dated Jan. 29, 2010 for U.S. Appl. No. 12/142,433 (8 pgs.).

Office Action dated May 24, 2011 for U.S. Appl. No. 12/142,433 (10 pgs.).

Office Action dated Apr. 30, 2010 for U.S. Appl. No. 12/141,191 (12 pgs.).

Office Action dated Oct. 27, 2009 for U.S. Appl. No. 12/142,120 (15 pgs.).

Office Action dated May 5, 2010 for U.S. Appl. No. 12/571,537 (12 pgs.).

Office Action dated Feb. 24, 2011 for U.S. Appl. No. 12/796,358 (13 pgs.).

Office Action dated Feb. 29, 2012 for U.S. Appl. No. 12/146,733 (8 pgs.).

Office Action dated Jun. 3, 2011 for U.S. Appl. No. 12/568,155 (11 pgs.).

IKA, "Introduction to IKA's Three Stage Dispax Reactor," Retrieved from <http://www.ikausa.com/pdfs/process/dr%202000-Homogenizing-Dispersing-Suspending-Emulsifying.pdf> on Aug. 22, 2012 (12 pgs.).

IKA-DRS Reactors website http://www.ikausa.com/dr.him, on Sep. 8, 2010 (2 pgs.).

Search Report and Written Opinion dated Feb. 13, 2013 for corresponding International Application No. PCT/US2012/045805 (14 pgs.).

METHOD AND SYSTEM FOR LIQUID PHASE REACTIONS USING HIGH SHEAR

STATEMENT REGARDING FEDERALLY SPONSORED RESEARCH OR DEVELOPMENT

Not Applicable.

BACKGROUND OF THE DISCLOSURE

1. Technical Field

Embodiments disclosed herein generally relate to systems and methods of producing C2+ hydrocarbons by way of liquid phase reactions and high shear effects. Other embodiments relate to conversion of reactants in a liquid medium to C2+ hydrocarbons, specifically alkanes, olefins, alcohols, aromatics, acids, and/or combinations thereof, by using high shear. Particular embodiments relate to a high shear process for improving conversion and reaction of CH4 to produce desired hydrocarbons.

2. Background

Various processes are known for the conversion of carbonaceous feedstock (e.g., coal, natural gas, etc.) to higher value liquid fuel or petrochemicals. Large quantities of methane, the main component of natural gas, are available in many areas of the world. Methane is an important building block in organic reactions used in industry as well as an important fuel and hydrogen source. The methane content of natural gas may vary within the range of from about 40 volume percent to about 95 volume percent. Other constituents of natural gas may include ethane, propane, butanes, pentane (and heavier hydrocarbons), hydrogen sulfide, carbon dioxide, helium and nitrogen.

Natural gas in liquid form has a density of 0.415 and a boiling point of minus 162° C. It is therefore not readily adaptable to transport as a liquid except for marine transport in very large tanks with a low surface to volume ratio. Large-scale use of natural gas often requires a sophisticated and extensive pipeline system. A significant portion of the known natural gas reserves is associated with remote fields, to which access is difficult. For many of these remote fields, pipelining to bring the gas to potential users is not economically feasible.

Economically transporting methane from remote areas by converting the gas to a liquid has long been sought in the industry. In addition, existing processes and production facilities for producing products from methane-based reactions are typically subject to various constraints, such as mass flow and product yield limitations and plant size and energy consumption requirements.

The effect of increasing carbon dioxide emission on global warming is also a major concern of scientists and governments due to its effect on the environment. The increased use of fossil fuels as a source of power and heat is thought by some to be a reason for the increase in carbon dioxide emissions. Oxidation of hydrocarbons is also common practice in chemical reactions such as the oxidation of ethylene. The products of combustion of hydrocarbons depend on the particular hydrocarbons but ultimately are carbon dioxide and water. Releasing large amounts of carbon dioxide into the atmosphere is hypothesized to have adverse effects, and there are efforts underway as a result, to reduce carbon dioxide emission overall.

Technologies to sequester carbon dioxide can consume large amounts of energy, derived in many cases from fossil fuels, which thus results in little or no net reduction in carbon dioxide. A net increase in carbon dioxide production is the result in some cases.

A process that allows the reuse of carbon dioxide to produce a valuable product such as fuel or chemical feedstock would be of great benefit in reducing the purported effects of carbon dioxide on global warming. It would be additionally beneficial to develop a process to convert carbon dioxide into a liquid fuel that can be transported and/or used as a feedstock for refinery or petrochemical processes.

Accordingly, in view of the art, there is a need for efficient and economical methods and systems for converting carbon-based components, such as carbon monoxide (CO) or carbon dioxide ($CO_2$) and/or low molecular weight alkanes, particularly methane (i.e., $CH_4$) to higher-value products. Such methods and systems should permit conversion of CO, $CO_2$, and/or $CH_4$, and provide increased selectivity and yield of high-value liquid and gas hydrocarbons (e.g., C2+). There is a need for methods and systems that allow economically favorable conditions of operating temperature, pressure, and/or reaction time, and a need in industry for improving production of liquid and gaseous hydrocarbons via reaction of CO, $CO_2$, and $CH_4$.

It has also been found that the use of the local reaction conditions obtainable under conditions of high fluid shear can be very effective with liquid and multiphase streams. The creation of zones of extreme temperatures and pressures may facilitate non-equilibrium reaction rates. Such local zones, with conditions far different from those of the bulk fluid(s) in a reaction system, could desirably be employed to achieve commercially significant production rates for processes that would otherwise be infeasible in conventional industrial processes. Thus, there is a need to provide systems and methods capable of providing favorable rates of reaction and high conversion based on non-equilibrium reaction conditions to produce high value liquid and multiphase products.

SUMMARY

Embodiments of the present disclosure pertain to a method of reacting one or more components in a liquid phase to form an organic product. The method may include the steps of feeding a carbon-based gas to a high shear device; feeding a hydrogen-based liquid medium to the high shear device; using the high shear device to form a dispersion that may include the carbon-based gas and the hydrogen-based liquid medium. The dispersion may include gas bubbles with a produce a stream that may include the organic product.

In an embodiment, the carbon-based gas may be carbon monoxide and the hydrogen-based liquid medium may be a Fischer-Tropsch liquid. In another embodiment, the carbon-based gas may be carbon dioxide and the hydrogen-based liquid medium may include methane. In other embodiments, the carbon-based gas may include carbon monoxide, and the hydrogen-based liquid medium may include methanol, an ether, or an oxide.

In some aspects, the organic product may include alkanes, olefins, aromatics, or combinations thereof. In other aspects, the organic product may include acetic acid.

The method may include the step of feeding hydrogen to the high shear device. In addition, the hydrogen-based liquid medium may include acetic acid, and the organic product may include ethanol. In some aspects, the method may also include utilizing a catalyst to promote the formation of the organic product. In an embodiment, the catalyst may be a hydrogenation catalyst. In another embodiment, the catalyst may be a carbonylation catalyst.

The high shear device may include a first rotor and a first stator operable together. The rotor and the stator may operate together to provide a tip speed of at least about 22.9 m/sec.

The revolution. In an embodiment, the high shear device may include a second rotor and a second stator proximate to each other and operable together. In another embodiment, the high shear device may operate to produce a local pressure of at least about 1034.2 MPa (150,000 psi) at the tip of a first rotor.

Other embodiments of the present disclosure pertain to a method of reacting a carbon-based component in a methane liquid phase to form an organic product. The method may include the steps of feeding the carbon-based gas to a high shear device that may have at least one inlet, at least one outlet, at least one generator configured with a first rotor and a first stator corresponding to the first rotor. The first rotor and the first stator may be separated by a gap width configured as the minimum distance between the first rotor and the first stator. The high shear mixing device may be capable of producing a tip speed of the first rotor of greater than 22 m/s. The method may further include the step(s) of feeding the methane liquid phase to the high shear device; using the high shear device to form a dispersion that may include the carbon-based gas and the hydrogen-based liquid medium; producing a localized temperature in the high shear device of at least about 125° C. to about 725° C.; and reacting the dispersion to produce a stream comprising the organic product.

The organic product may include at least one of alkanes, olefins, aromatics, and combinations thereof. In an embodiment, the carbon-based component may include carbon monoxide gas. In another embodiment, the carbon-based component may include carbon dioxide gas.

Yet other embodiments of the present disclosure pertain to a system for improving the conversion of a hydrogen-based component to produce an organic product. The system may include at least one high shear mixing device having at least one inlet, at least one outlet, at least one generator configured with a first rotor and a first stator corresponding to the first rotor; a reactor comprising a reactor inlet and a reactor outlet; and a pump configured for delivering a liquid medium via said at least one inlet to the high shear mixing device.

In some aspects, the first rotor and the first stator may be separated by a gap width configured as the minimum distance between the first rotor and the first stator. The high shear mixing device is capable of producing a tip speed of the first rotor of greater than 22 m/s. The high shear device may be operable to produce a localized temperature range of at least about 125° C. In another embodiment, the high shear device may operate to produce a local pressure of at least about 1034.2 MPa (150,000 psi) and a local temperature of at least 500° C. at the tip of a first rotor.

In other aspects, high shear mixing device may include a second generator configured with a second rotor and a second stator corresponding to the second rotor. The high shear mixing device may include a catalytic surface.

Certain embodiments of an above-described methods or systems potentially provide for more optimal time, temperature and pressure conditions than are otherwise possible, and which potentially increase the rate of the multiphase process. Certain embodiments of the above-described methods or systems potentially provide overall cost reduction by operating at lower temperature and/or pressure, providing increased product per unit of catalyst consumed, decreased reaction time, and/or reduced capital and/or operating costs. These and other embodiments and potential advantages will be apparent in the following detailed description and drawings.

BRIEF DESCRIPTION OF THE DRAWINGS

For a more detailed description of the preferred embodiment of the present disclosure, reference will now be made to the accompanying drawings, wherein.

NOTATION AND NOMENCLATURE

Figure 1:
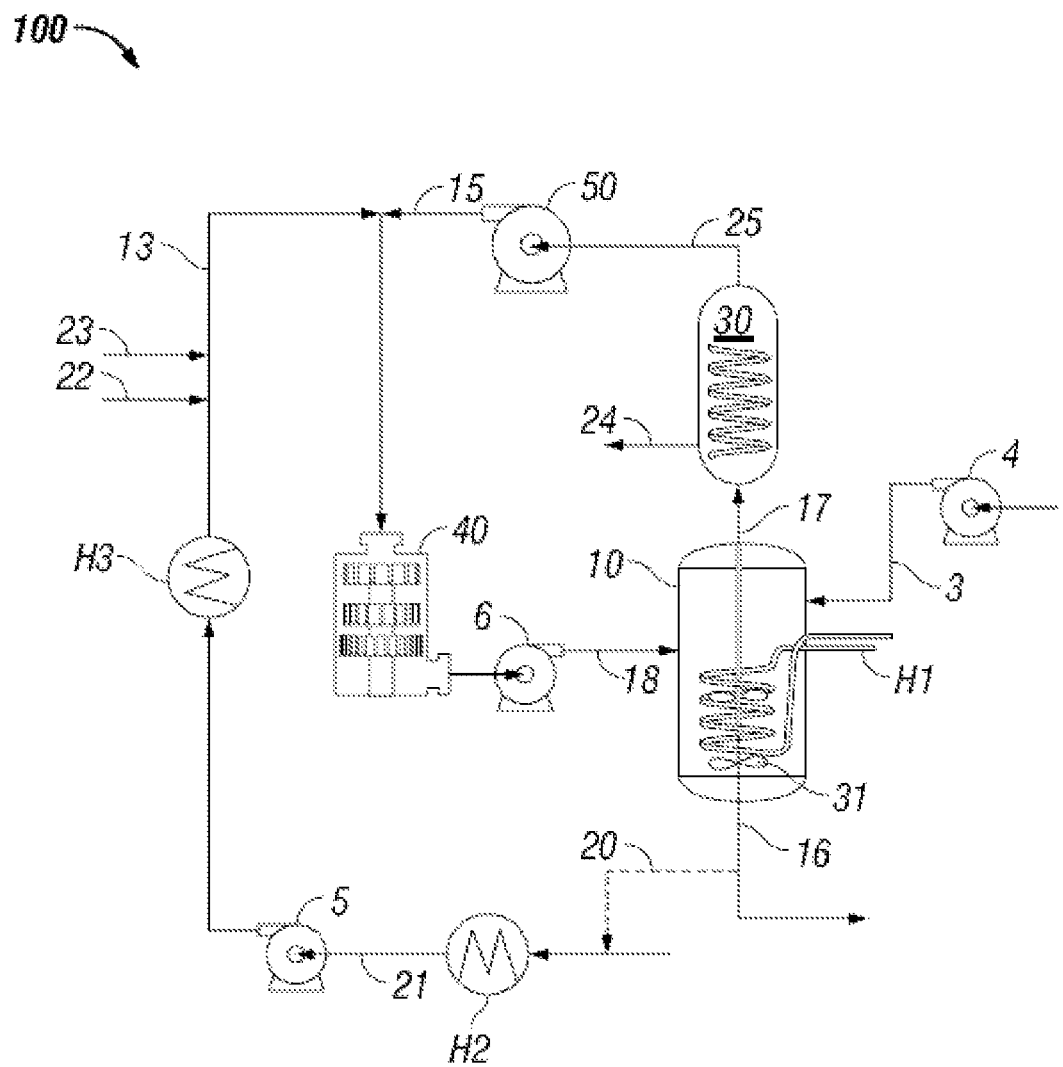
FIG. 1 is a schematic of a reaction system according to embodiments of this disclosure comprising high shear dispersing.

As used herein, the term "dispersion" refers to a multiphase mixture that contains at least two distinguishable phases, which may comprise different substances, that will not readily mix and dissolve together. As used herein, a "dispersion" comprises a "continuous" phase (or "matrix"), which holds therein discontinuous droplets, bubbles, and/or particles of another phase or substance. The term dispersion may thus refer to foams comprising gas bubbles suspended in a liquid continuous phase, emulsions in which droplets of a first liquid are dispersed throughout a continuous phase comprising a second liquid with which the first liquid is immiscible, and continuous liquid phases throughout which solid particles are distributed.

As used herein, the term "dispersion" encompasses continuous liquid phases throughout which gas bubbles are distributed, continuous liquid phases throughout which solid particles (e.g., solid catalyst) are distributed, continuous phases of a first liquid throughout which droplets of a second liquid that is substantially insoluble in the continuous phase are distributed, and liquid phases throughout which any one or a combination of solid particles, immiscible liquid droplets, and gas bubbles are distributed. Hence, a dispersion can exist as a homogeneous mixture in some cases (e.g., liquid/liquid phase), or as a heterogeneous mixture (e.g., gas/liquid, solid/liquid, or gas/solid/liquid), depending on the nature of the materials selected for combination. A dispersion may comprise, for example, bubbles of gas (e.g. CO gas) and/or particles of carbonaceous material in a liquid phase (e.g. slurry liquid and/or liquid hydrocarbons)

The term "oxygenate" is used herein to refer to substances that have been infused with oxygen. For example, the term refers to any oxygen comprising hydrocarbon such as high octane gasoline or diesel, suitable to drive combustion engines, as well as to oxygenated fuels sometimes employed as gasoline additives to reduce carbon monoxide that is created during the burning of the fuel. The term "oxygenate" includes, but is not limited to, aldehydes such as formaldehyde, methyl formate, and formic acid as well as oxygenates based on alcohols including: methanol, ethanol, isopropyl alcohol, n-propyl alcohol, n-butanol, 2-ethyl hexanol, furfuryl alcohol, benzyl alcohol, isobutyl alcohol, and gasoline grade t-butanol (GTBA). Other oxygenates include carbonyl compounds such as ketones, esters, amides and anhydrides.

The terms "simple alkane" and "low molecular weight alkane" are used herein to refer to low carbon number alkanes including methane, propane, butane, etc., which are gaseous at room temperature and atmospheric pressure.

The term "light gas" as utilized herein refers to, by way of example, a gas such as CO, CO2, simple alkanes having from one to five carbon atoms, or a combination thereof.

Terms or phrases, such as "hydrogen source", "hydrogen component", "hydrogen-based", "hydrocarbonaceous", etc., as utilized herein refers to, by way of example, a component or molecule having at least one hydrogen atom, such as H2, H2O, or CH4.

Terms or phrases, such as "carbon source", "carbon component", "carbon-based", "carbonaceous", etc., as utilized herein refers to, by way of example, a component or molecule having at least one carbon atom, such as CO or CO2.

Use of the phrase, 'all or a portion of' used herein to mean 'all or a percentage of the whole' or 'all or some components of.'

The term "catalytic surface" is used herein to refer to a surface in a device that is constructed with catalytic material (such as metals, alloys, etc.) so that catalytic activity is manifested when suitable substance comes in touch with said catalytic surface. The use of the term "catalytic surface" in this document includes all such surfaces regardless of the shape and size of surface, material of construct, method of make, degree of activity, or purpose of use.

The term "multifunctional catalyst" is used herein to refer to a catalyst that has more than one function of promoting two or more reactions when necessary reactants are present. For example, such multifunctional catalyst is a blend of two compatible catalysts wherein one catalyst promotes Fischer-Tropsch reactions and the other promotes alcohol forming reactions.

Certain terms are used throughout the following description and claims to refer to particular system components. This document does not intend to distinguish between components that differ in name but not function. In the following discussion and in the claims, the terms "including", "having", and "comprising" are used in an open-ended fashion, and thus should be interpreted to mean "including, but not limited to . . . "

DETAILED DESCRIPTION

Overview

The rate of chemical reactions involving liquids, gases, and solids depends in part on time of contact, temperature, and pressure. In cases where it is desirable to react two or more raw materials of different phases (e.g., solid and liquid; liquid and gas; solid, liquid and gas), one of the limiting factors on the overall rate of reaction can be mass transfer limitations on the contact time of the reactants. In the case of heterogeneously catalyzed reactions there is the additional mass transfer limitation related to transport of the reaction products from the surface of the catalyst to permit the catalytic sites to catalyze further reactants. Contact time for the reactants and/or catalyst may be controlled by mixing which provides contact with two or more reactants at a reactive site involved in a chemical reaction.

A reactor system or process that comprises an external high shear device or mixer as described herein makes possible reduced mass transfer limitations and thereby allows the reaction to more closely approach kinetic limitations. When overall reaction rates are thus accelerated, residence times of reactants and products may be decreased, thereby increasing obtainable throughput. Product yield may be increased as a result of the high shear system and process. Alternatively, if the product yield of an existing process is acceptable, decreasing the required residence time by incorporation of suitable high shear may allow for the use of lower temperatures and/or pressures than conventional processes.

Without wishing to be limited by theory, it is believed that the high shear conditions provided by a reactor system or process that comprises an external high shear device or mixer as described herein may permit conversion of various ingredients/reactants into liquid hydrocarbons generally having five or more carbon atoms (C5+ hydrocarbons) and gaseous hydrocarbons generally having two or more carbon atoms (C2+ hydrocarbons) at conditions under which reaction may not conventionally be expected to occur to any significant extent.

As such, embodiments disclosed herein provide innovative technology to produce organic products comprising C2+ hydrocarbons, such as alkanes, olefins, alcohols, acids, and aromatics, from gaseous or liquid reactants, such as CO and/or simple alkanes like CH4. For example, a light gas with CO may be intimately mixed with a CH4-based liquid medium. Either of the light gas and the liquid medium may serve as hydrogen source, which may include, for example, water and/or hydrocarbons. A high shear reactor system, and optionally a catalyst, may dissociate reactants into free radicals allowing them to reform into product comprising hydrocarbons.

In an embodiment, the method may include contacting the mixture with a catalyst that promotes the formation of synthesis gas. In an embodiment, the method further comprises recycling separated unreacted carbonaceous material, separated liquid medium or both. In an embodiment, the carbonaceous material comprises coke, coal, peat, natural gas, or a combination thereof. In some cases, the coal is selected from the group consisting of bituminous, anthracite, and lignite. In an embodiment, the carbonaceous material comprises powdered coal or coalbed methane.

In an embodiment, the method may include utilizing at least a portion of synthesis gas to produce a liquid product by first forming a dispersion of synthesis gas in a liquid phase. In an embodiment, utilizing at least a portion of the synthesis gas to produce a liquid product may include catalytically reacting the at least a portion of the synthesis gas to produce Fischer-Tropsch hydrocarbons. In an embodiment, the liquid product comprises liquid hydrocarbons and/or alcohols. In an embodiment, the liquid product may be primarily liquid hydrocarbons, primarily alcohols, or substantially equivalent amounts of alcohols and liquid hydrocarbons. In an embodiment, the liquid phase may be one or more liquid hydrocarbon produced by Fischer-Tropsch, one or more alcohol, or a combination thereof. In an embodiment, the method of forming a dispersion may include introducing the synthesis gas and liquid carrier into a high shear device comprising at least one rotor and at least one stator and providing a pre-determined rotor tip speed.

In an embodiment, a feed gas may be synthesis gas. In some cases, the synthesis gas may be generated via natural gas reforming. In other cases, the synthesis gas may be generated via solids gasification. In an embodiment, the solid is selected from the group consisting of coal, biomass, and bio-renewables.

In an embodiment, the multifunctional catalyst promotes Fischer-Tropsch reactions. In an embodiment, the multifunctional catalyst promotes dehydrogenation reactions. In an embodiment, the multifunctional catalyst promotes alcohol forming reactions. In an embodiment, the multifunctional catalyst promotes at least two of the following reactions: dehydrogenation, water dissociation, carbon dioxide dissociation, syngas reforming, and alcohol synthesis. In an embodiment, the high shear device comprises a catalytic surface.

Embodiments disclosed herein may provide a system and process for the production of hydrocarbons and/or oxygenates from light gas having CO2 dioxide and/or at least one C1-C5 alkane using at least one high shear reactor device to dissociate reactor feedstock into free radicals by providing intimate contact of reactants and promoting chemical reactions between multiphase reactants. The resulting hydrogen and/or oxygen radicals may react with carbon dioxide and/or alkane to yield a product of hydrocarbons and/or oxygenates. The high shear device makes favorable reaction(s) that may not be favorable using conventional reactors and/or operating conditions (i.e.

In one embodiment, the process may include providing water and CO2 gas into a high shear reactor. Within the high shear reactor system the water and carbon dioxide may be dissociated into components. Subsequently, the components recombine to produce a product comprising higher carbon number (i.e., $C_{2+}$, preferably $C_5$-$C_{10}$) hydrocarbons and/or oxygenates. The process may include the use of at least one high shear device to provide for production of oxygenates and/or hydrocarbons without the need for large volume reactors. In embodiments, the addition of water serves to assist in steam stripping of organics present in a vessel.

Other aspects of the disclosure may pertain to a process for production of hydrocarbons and/or oxygenates from carbon dioxide and/or methane and a source of hydrogen such as simple hydrocarbons or other hydrocarbon source. Water may also optionally or additionally be present as a source of free hydrogen and hydroxyl radicals. In embodiments of the method, the hydrogen source may be selected from water, lower alkanes, and combinations thereof. Reactions may be catalyzed with catalytic compounds known to act as dehydrogenation catalyst. In embodiments, the hydrogen source may be a gas, e.g., hydrogen gas, or hydrogen dissociated in HSD 40 from simple gaseous alkane and the liquid in line 21 may be a carrier, such as poly ethylene glycol.

The systems and processes disclosed may include the use of high shear technology for the conversion of CO, CO2, and/or hydrocarbons to desirable C2+ hydrocarbons, such as alkanes, olefins, alcohols, acids, aromatics, or combinations thereof. The production of hydrocarbon products in accordance with the disclosure employs a high shear mechanical device to provide rapid contact and mixing of chemical ingredients in a controlled environment in a high shear device. The use of at least one high shear device reduces mass transfer limitations on the reaction(s) thus increasing rates of mass transfer and enabling reactions to more closely approach kinetic limitations and also producing localized non-ideal conditions that permit reactions to occur that would not otherwise be expected to occur based on Gibbs free energy predictions, as discussed further herein below.

Resultant hydrocarbons or hydrocarbon mixtures products may be suitable for driving conventional combustion engines or for further industrial processing or other commercial use. Intermediate products such as methanol or dimethyl ether may also be generated and used. The high shear device makes favorable reaction(s) that may not be favorable using conventional reactors and/or operating conditions (i.e.

High shear systems and methods usable to provide favorable conditions for reaction of one or more liquid phase (or mixtures) reactants to produce desirable liquid and/or gaseous hydrocarbons are disclosed. The system and method may be used to produce hydrocarbons or hydrocarbon mixtures suitable for driving conventional combustion engines or hydrocarbons suitable for further industrial processing or other commercial use. Intermediate products may also be generated by the embodiments disclosed herein. In embodiments the systems and methods may provide for the conversion of reactants selected from CO, CO2, H2, CH4, acetic acid, methanol (MeOH [or reactive derivatives]), and combinations thereof to hydrocarbons with carbon numbers greater than or equal to 2 (i.e., C2+), such as $C_5$-$C_{10}$ alkanes, olefins, alcohols, acids, and/or aromatics. Reactions may be carried out with or without catalyst, and may include other feedstock ingredients, such as water.

In accordance with certain embodiments, a method of reacting one or more components in a liquid phase to form a product stream that includes feeding at least one carbon-based component to a high shear device; feeding at least one liquid medium to the high shear device; using the high shear device to form a dispersion comprising the at least one carbon component and the at least one liquid medium; and reacting the dispersion to produce the product stream comprising C2+ hydrocarbons. The method may include providing the dispersion into a reactor. Reacting the dispersion may occur in the shear device, the reactor, or both.

The carbon-based component may include at least one of CO, CO2, acetic acid, and combinations thereof, the liquid medium may include at least one of a hydrocarbon-based component, water, and combinations thereof, and the C2+ hydrocarbons product stream may include at least one of alkanes, olefins, alcohols, aromatics, carboxylic acid, and combinations thereof.

The method may also include the carbon-based component in a gaseous state, such that the dispersion may include gas bubbles dispersed in the liquid medium whereby the dispersion has be in the range of at least in a shear gap of the high shear device.

Catalyst and/or solvent may be fed to the high shear device. The high shear device may also include a catalytic surface. The high shear device may be configured with a first rotor and a first stator operable together. In embodiments, the configuration of the first rotor and the first with D as the diameter of the first rotor and n as the frequency of revolution. In other embodiments, the high shear device may include a second rotor and a second stator proximate to each other and operable together.

Other embodiments include a system for reacting two or more reactants in a liquid medium to form a product stream that includes at least one high shear mixing device with at least one inlet, at least one outlet, and at least one generator having a first rotor and a first stator corresponding to the first rotor. The first rotor and the first stator may be separated by a gap width configured as the minimum distance between the first rotor and the first stator. In embodiments the gap width may be in the range of about 0.02 mm to 5 mm. The system may further include a reactor having a reactor inlet and a reactor outlet, and a pump configured for delivering a fluid stream via the at least one inlet to the high shear mixing device.

The high shear mixing device may be capable of producing a tip speed of the first rotor in excess of 22 m/s. The high shear mixing device may also include a second generator configured with a second rotor and a second stator corresponding to the second rotor, and may also include catalyst or a catalytic surface.

The first reactant may include at least one of CO, CO2, acetic acid, MeOH, and combinations thereof, present in the liquid medium, and a second reactant may include a hydrocarbon, hydrogen, water, and combinations thereof. The system may include the high shear device operating at and/or producing a localized temperature therein. In an embodiment, the local temperature is in the range of about 125° C. to about 725° C.

Yet other embodiments disclosed herein provide for a method for CO and CH4 to C2+ hydrocarbons that includes forming a liquid phase mixture comprising CO gas and a liquid medium comprising a hydrocarbon; subjecting the liquid phase mixture to a shear rate greater than 20,000 s$^{-1}$ to produce a dispersion of CO gas bubbles in the liquid medium; and introducing the dispersion into a reactor from which a reactor product stream comprising C2+ hydrocarbons is removed. The C2+ hydrocarbons product stream may include at least one of alkanes, olefins, aromatics, and combinations thereof.

The method may include feeding a catalyst to the high shear device, and further forming the liquid phase mixture comprising a solvent, such that the produced dispersion may also include unreacted catalyst and the solvent. The dispersion may include an average bubble The step of subjecting the liquid phase mixture to a shear rate greater than 20,000 $s^{-1}$ may further include introducing the liquid phase mixture into a high shear device comprising at least two rotor-stator generators. The at least one of the at least two rotor-stator generators may include a first rotor and a first stator proximate to the first rotor, whereby the first rotor and the first stator are separated by a gap width. The gap width may be the minimum distance between the first rotor and the first stator, and the gap width may be in the range of about 0.02 mm to about 5 mm. In embodiments, the high shear device may be operable to produce a localized temperature between the rotor and the stator of at least 125° C.

System for Production of Organics

A high shear system for the production of hydrocarbons will now be described in relation to FIG. 1, which is a process flow diagram of a representative high shear system 100 for the production of organics via conversion of gas and/or liquid reactants. The basic components of a representative system include external high shear mixing device (HSD) 40, vessel 10, and pump 5. As shown in FIG. 1, high shear device 40 is located external to vessel/reactor 10. Each of these components is further described in more detail below. Line 21 is a feed line connected to pump 5 for introducing liquid medium to system 100.

Line 13 connects pump 5 to HSD 40, and line 18 connects HSD 40 to vessel 10. One or more line may be connected to line 13 for introducing reactant gas or liquids (e.g., CO and/or CH4 gas). As shown in the embodiment in FIG. 1, lines 22 and 23 are connected to line 13. Alternatively, lines 22 and/or 23 may be connected to an inlet of HSD 40. Line 17 may be connected to vessel 10 for removal of unreacted reactant gas and/or reaction product gases. Product outlet line 16 is connected to vessel 10 for removal of liquids from vessel 10. In embodiments, product line 16 may be connected to line 21 or line 13, to provide for multi-pass operation, if desired.

Additional components may be incorporated between vessel 10, external HSD 40, and pump 5 in some applications of the process, as will become apparent upon reading the description of the high shear process for production of organic product described herein below. For example, high shear system 100 may further comprise condenser 30, compressor 50, feed pump 4, high pressure pump 6, or any combination thereof. As shown in FIG. 1, high shear system 100 may further comprise one or more additional pumps, such booster pump 6, or other pumps as necessary. Heat exchangers may be positioned throughout system 100. In embodiments, temperature control equipment is internal to vessel 10, or positioned on a line within system 100. For example, in the embodiment of FIG. 1, heat exchanger H1 is associated with vessel 10, heat exchanger H2 is positioned on line 21, and heat exchanger H3 is positioned on line 13. A heat exchanger may be positioned on line 16 of vessel 10 and may serve to adjust the temperature of reaction products exiting vessel 10.

High Shear Mixing Device.

External high shear mixing device (HSD) 40, also sometimes referred to as a high shear device or high shear mixing device, is configured for receiving an inlet stream, via line 13, which may include a liquid medium and a light gas of various compositions. Alternatively, HSD 40 may be configured for receiving streams (e.g., liquid and/or gas phase) via separate inlet lines (not shown). Although only one high shear device is shown in FIG. 1, it should be understood that some embodiments of the system may have two or more high shear mixing devices arranged either in series or parallel flow.

HSD 40 is a mechanical device that utilizes one or more generators comprising a rotor/stator combination, each of which may have a shear gap between the stator and rotor. The gap between the rotor and the stator in each generator set may be fixed or may be adjustable. HSD 40 is configured in such a way that it is capable of producing submicron and micron-sized bubbles in a reactant mixture flowing through the high shear device. The high shear device comprises an enclosure or housing so that the pressure and temperature of the reaction mixture may be controlled.

High shear mixing devices are generally divided into three general classes, based upon their ability to mix fluids. Mixing is the process of reducing the size of particles or inhomogeneous species within the fluid. One metric for the degree or thoroughness of mixing is the energy density per unit volume that the mixing device generates to disrupt the fluid particles. The classes are distinguished based on delivered energy densities. Three classes of industrial mixers having sufficient energy density to consistently produce mixtures or emulsions with particle sizes in the range of submicron to 50 microns include homogenization valve systems, colloid mills and high speed mixers. In the first class of high energy devices, referred to as homogenization valve systems, fluid to be processed is pumped under very high pressure through a narrow-gap valve into a lower pressure environment. The pressure gradients across the valve and the resulting turbulence and cavitation act to break-up any particles in the fluid. These valve systems are most commonly used in milk homogenization and can yield average particle sizes in the submicron to about 1 micron range.

At the opposite end of the energy density spectrum is the third class of devices referred to as low energy devices. These systems usually have paddles or fluid rotors that turn at high speed in a reservoir of fluid to be processed, which in many of the more common applications is a food product. These low energy systems are customarily used when average particle sizes of greater than 20 microns are acceptable in the processed fluid.

Between the low energy devices and homogenization valve systems, in terms of the mixing energy density delivered to the fluid, are colloid mills and other high speed rotor-stator devices, which are classified as intermediate energy devices. A typical colloid mill configuration includes a conical or disk rotor that is separated from a complementary, liquid-cooled stator by a closely-controlled rotor-stator gap, which is commonly between 0.0254 mm to 10.16 mm (0.001-0.40 inch). Rotors are usually driven by an electric motor through a direct drive or belt mechanism. As the rotor rotates at high rates, it pumps fluid between the outer surface of the rotor and the inner surface of the stator, and shear forces generated in the gap process the fluid. Many colloid mills with proper adjustment achieve average particle sizes of 0.1-25 microns in the processed fluid. These capabilities render colloid mills appropriate for a variety of applications including colloid and oil/water-based emulsion processing such as that required for cosmetics, mayonnaise, or silicone/silver amalgam formation, to roofing-tar mixing.

Tip speed is the circumferential distance traveled by the tip of the rotor per unit of time. Tip speed is thus a function of the rotor diameter and the rotational frequency. Tip speed (in meters per minute, for example) may be calculated by multiplying the circumferential distance frequency of revolution (for example revolutions per minute, rpm). A colloid mill, for example, may have a tip speed in excess of 22.9 m/s (4500 ft/min) and may exceed 40 m/s (7900 ft/min). For the purpose of this disclosure, the term 'high shear' refers to mechanical rotor stator devices (e.g., colloid mills or rotor-stator dispersers) that are capable of tip speeds in excess of 5.1 m/s. (1000 ft/min) and require an external mechanically driven power device to drive energy into the stream of products to be reacted. For example, in HSD 40, a tip speed in excess of 22.9 m/s (4500 ft/min) is achievable, and may exceed 40 m/s (7900 ft/min). In some embodiments, HSD 40 is capable of delivering at least 300 L/h at a tip speed of at least 22.9 m/s (4500 ft/min). The power consumption may be about 1.5 kW. HSD 40 combines high tip speed with a very small shear gap to produce significant shear on the material being processed. The amount of shear will be dependent on the viscosity of the fluid.

Accordingly, a local region of elevated pressure and temperature is created at the tip of the rotor during operation of the HSD 40. Alternatively, the local region of elevated pressure and temperature is created in the shear gap formed between any rotor and stator during operation of the HSD 40. In some cases the locally elevated pressure is at least about 1034.2 MPa (150,000 psi). In some cases the locally elevated temperature is at least 500° C. In an embodiment, the locally elevated temperature is in the range of about 125° C. to about 725° C. In some cases, these local pressure and temperature elevations may persist for nano or pico seconds. The localized temperature and pressure conditions within HSD 40 may be suitable to promote any of the reactions disclosed herein. Thus, HSD 40 may be functional as a reactor.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the reactants. In embodiments, the energy expenditure of HSD 40 is greater than 1000 W/m$^3$. In embodiments, the energy expenditure of HSD 40 is in the range of from about 3000 W/m$^3$ to about 7500 W/m$^3$.

The shear rate is the tip speed divided by the shear gap width (minimal clearance between the rotor and stator). The shear rate generated in HSD 40 may be in the greater than 20,000 s$^{-1}$. In some embodiments the shear rate is at least 40,000 s$^{-1}$. In some embodiments the shear rate is at least 100,000 s$^{-1}$. In some embodiments the shear rate is at least 500,000 s$^{-1}$. In some embodiments the shear rate is at least 1,000,000 s$^{-1}$. In some embodiments the shear rate is at least 1,600,000 s$^{-1}$. In embodiments, the shear rate generated by HSD 40 is in the range of from 20,000 s$^{-1}$ to 100,000 s$^{-1}$. For example, in one application the rotor tip speed is about 40 m/s (7900 ft/min) and the shear gap width is 0.0254 mm (0.001 inch), producing a shear rate of 1,600,000 s$^{-1}$. In another application the rotor tip speed is about 22.9 m/s (4500 ft/min) and the shear gap width is 0.0254 mm (0.001 inch), producing a shear rate of about 901,600 s$^{-1}$.

HSD 40 is capable of dispersing or transporting light gas into a main liquid phase (continuous phase) with which it would normally be immiscible. The liquid phase may be a mixture that includes at least one hydrogen source (e.g. simple liquid hydrocarbon, such as CH$_4$, and/or water). In embodiments, the liquid phase may include a catalyst mixed therewith. In some embodiments, HSD 40 comprises a colloid mill. Suitable colloidal mills are manufactured by IKA® Works, Inc. Wilmington, N.C. and APV North America, Inc. Wilmington, Mass., for example. In some instances, HSD 40 comprises the Dispax Reactor® of IKA® Works, Inc.

The high shear device comprises at least one revolving element that creates the mechanical force applied to the reactants or other inlet streams. The high shear device comprises at least one stator and at least one rotor separated by a clearance. For example, the rotors may be conical or disk shaped and may be separated from a complementarily-shaped stator. In embodiments, both the rotor and stator comprise a plurality of circumferentially-spaced teeth. In some embodiments, the stator(s) are adjustable to obtain the desired shear gap between the rotor and the stator of each generator (rotor/stator set). Grooves between the teeth of the rotor and/or stator may alternate direction in alternate stages for increased turbulence. Each generator may be driven by any suitable drive system configured for providing the necessary rotation.

In some embodiments, the minimum clearance (shear gap width) between the stator and the rotor is in the range of from about 0.0254 mm (0.001 inch) to about 3.175 mm (0.125 inch). In certain embodiments, the minimum clearance (shear gap width) between the stator and rotor is about 1.52 mm (0.060 inch). In certain configurations, the minimum clearance (shear gap) between the rotor and stator is at least 1.78 mm (0.07 inch). The shear rate produced by the high shear device may vary with longitudinal position along the flow pathway. In some embodiments, the rotor is set to rotate at a speed commensurate with the diameter of the rotor and the desired tip speed. In some embodiments, the high shear device has a fixed clearance (shear gap width) between the stator and rotor. Alternatively, the high shear device has adjustable clearance (shear gap width).

In some embodiments, HSD 40 comprises a single stage dispersing chamber (i.e., a single rotor/stator combination, a single generator, etc.). In some embodiments, high shear device 40 is a multiple stage inline disperser and comprises a plurality of generators. In certain embodiments, HSD 40 comprises at least two generators. In other embodiments, high shear device 40 comprises at least 3 high shear generators. In some embodiments, high shear device 40 is a multi-stage mixer whereby the shear rate (which, as mentioned above, varies proportionately with tip speed and inversely with rotor/stator gap width) varies with longitudinal position along the flow pathway, as further described herein below.

In some embodiments, each stage of the external high shear device has interchangeable mixing tools, offering flexibility. For example, the DR 2000/4 Dispax Reactor® of KA® Works, Inc. Wilmington, N.C. and APV North America, Inc. Wilmington, Mass., comprises a three stage dispersing module. This module may comprise up to three rotor/stator combinations (generators), with choice of fine, medium, coarse, and super-fine for each stage. This allows for creation of dispersions having a narrow distribution of the desired bubble size (e.g., light gas bubbles). In some embodiments, each of the stages is operated with super-fine generator. In some embodiments, at least one of the generator sets has a rotor/stator minimum clearance (shear gap width) of greater than about 5.0 mm (0.20 inch). In alternative embodiments, at least one of the generator sets has a minimum rotor/stator clearance of greater than about 1.78 mm (0.07 inch).

Vessel.

Once dispersed (i.e., formed, mixed, etc.), the dispersion exits HSD 40 via high shear device outlet dispersion line 18 and is introduced into vessel 10. Vessel 10 may comprise any type of reactor in which multiphase reaction can be propagated to carry out the conversion reaction(s). For instance, a continuous or semi-continuous stirred tank reactor, or one or more batch reactors may be employed in series or in parallel. In some embodiments, vessel 10 is a tower reactor. In some applications, vessel 10 is a tubular reactor, and in others a tubular reactor or multi-tubular reactor.

Any number of reactor inlet lines is envisioned, such as inlet line 3 shown in FIG. 1. An inlet line may be connected to vessel 10 for receiving a catalyst solution or slurry during operation of the system with heterogeneous catalyst. In embodiments, water is injected into vessel 10 to assist in steam stripping of organics present within vessel 10. In this manner, a portion of the organic product may be stripped with steam and exit vessel 10 in line 17 rather than in line 16. Vessel 10 may comprise an exit line 17 for vent gas, and an outlet product line 16 for a product stream. In embodiments, vessel 10 comprises a plurality of reactor product lines 16.

Conversion of reactants to C2+ hydrocarbons will occur wherever suitable time, temperature and pressure conditions exist. For example, such as in the HSD 40, the vessel 10, and/or both the HSD 40 and the vessel 10. The reaction carried out by high shear system 100 may comprise a homogeneous catalytic reaction in which the catalyst is in the same phase as another component of the reaction mixture or a heterogeneous catalytic reaction involving a solid catalyst. A discrete reactor/vessel 10 is often desirable to allow for increased residence time, agitation and heating and/or cooling, as well as for separation and recovery of volatile reaction products and recycling of non-reacted gases. When a fixed bed reactor 10 is utilized, the reactor/vessel 10 may become the primary location for the reaction to occur.

Vessel 10 outlet line 16 may be fluidly connected to line 21, for example via line 20, for recycle of a portion of the contents in line 16 comprising liquid product to HSD 40. Alternatively, a separate outlet line may connect vessel 10 with line 21 in some embodiments. In FIG. 1, high shear system 100 is configured for recycle of a portion of line 16. This configuration is one which lends itself to multi-pass operation, for example.

Vessel 10 may include one or more of the following components: stirring system, temperature control capabilities, pressure measurement instrumentation, temperature measurement instrumentation, one or more injection points, and level regulator (not shown), as are known in the art of reaction vessel design. As shown in the embodiment of FIG. 1, vessel 10 may further comprise stirring system 31; heating and/or cooling capabilities H1, pressure measurement instrumentation, temperature measurement instrumentation, or a combination thereof. For example, stirring system 31 may include a motor driven mixer. A temperature control apparatus H1 may comprise, for example, a heating mantle or cooling coils. Alternatively, as much of the conversion reaction may occur within HSD 40 in some embodiments, vessel 10 may serve primarily as a storage vessel in some cases. Although generally less desired, in some applications vessel 10 may be omitted, particularly if multiple high shear devices/reactors are employed in series, as further described below.

In an embodiment, the reactor may be a Fischer-Tropsch reactor, a fixed-bed reactor, or a slurry reactor. In an embodiment, the reactor may include a multifunctional catalyst. In an embodiment, the multifunctional catalyst may promote both Fischer-Tropsch reactions and alcohol forming reactions or both dehydrogenation reactions and alcohol forming reactions. In an embodiment, the multifunctional catalyst may promote at least two of the following reactions: dehydrogenation, water dissociation, carbon dioxide dissociation, syngas reforming, and alcohol synthesis. In an embodiment, the high shear mixing device of the system may include a catalytic surface.

Heat Transfer Devices.

In addition to the above-mentioned heating/cooling capabilities of vessel 10, other external or internal heat transfer devices for heating or cooling a process stream are also contemplated in variations of the embodiments illustrated in FIG. 1. For example, temperature control may be provided to vessel 10 via internal heat transfer devices as known to one skilled in the art. The use of external heating and/or cooling heat transfer devices is also contemplated. Some suitable locations for one or more such heat transfer devices are between pump 5 and HSD 40, between HSD 40 and vessel 10, and between vessel 10 and pump 5 when system 100 is operated in multi-pass mode. Some non-limiting examples of such heat transfer devices are shell, tube, plate, and coil heat exchangers, as are known in the art.

In the embodiment of high shear system 100 in FIG. 1, three heat transfer devices are used to control temperature throughout the system. Heat transfer device H1 is used to control the temperature of the product in vessel 10. Heat transfer device H2 is positioned on line 21 for controlling temperature in line 21. Heat transfer device H3 serves to control the temperature of line 13 and thereby control the temperature of the inlet feedstream to HSD 40. Use and configuration of heating/cooling devices is for the purpose of carrying out the desired reaction and may be altered accordingly as known to those of skill in the art.

Separator (Not Shown).

Embodiments of the disclosure may include the use of a separation device, which may be any apparatus suitable to provide separatory effects of any resultant product streams. Thus, the separator may be, for example, selected from hydrocyclones, gravity separators, filters, and magnetic separators. In some embodiments, the separator may be a distillation column, whereby liquid hydrocarbons and liquid charge may be separated from Fischer-Tropsch catalyst. In embodiments where gas is removed with liquid hydrocarbon product in line 16, an additional separator may serve to separate gaseous product and unreacted ingredients from liquid hydrocarbon product and liquid medium. Unreacted ingredients may be separated from low-boiling gaseous hydrocarbon and recycled to HSD 40. If the product in line 16 comprises catalyst, the hydrocarbon product may then be introduced into the separator for removal of catalyst stream from the liquid hydrocarbon product.

Operations.

Pump 5 is configured for either continuous or semi-continuous operation, and may be any suitable pumping device that is capable of providing greater than 202.65 kPa (2 atm) pressure, alternatively greater than 303.975 kPa (3 atm) pressure, to allow controlled flow through HSD 40 and system 100. For example, a Roper Type 1 gear pump, Roper Pump Company (Commerce Ga.) Dayton Pressure Booster Pump Model 2P372E, Dayton Electric Co (Niles, Ill.) is one suitable pump. All contact parts of the pump may comprise stainless steel, for example, 316 stainless steel. In some embodiments of the system, pump 5 is capable of pressures greater than about 2026.5 kPa (20 atm). In embodiments, pump 5 produces a flow rate of liquid medium 12 of between about 0.5 and about 1 gallon/min. In embodiments, pump 5 produces a flow rate of liquid medium 12 of about 1 gallon/min.

In addition to pump 5, one or more additional, high pressure pump (not shown) may be included in the system illustrated in FIG. 1. For example, a booster pump, which may be similar to pump 5, may be included between HSD 40 and vessel 10 for boosting the pressure into vessel 10. In the embodiment of FIG. 1, high shear system 100 further comprises a high pressure pump 6 for boosting the pressure into vessel 10. When pump 6 is incorporated as a booster pump, pump 5 may be used as a throttling pump/valve to reduce pressure to the high shear unit, thus reducing wear thereof. As still another example, a compressor type pump 50 may be positioned between line 17 and HSD 40 for recycling gas from vessel 10 to an inlet of the high shear device.

As another example, a supplemental feed pump, which may be similar to pump 5, may be included for introducing additional reactants or catalyst into reactor 10, for example, via line 15. In the embodiment of FIG. 1, for example, supplemental feed pump 4 is used to introduce additional raw materials into vessel 10 through injection line 3. Catalyst and make-up fluids may be periodically or continuously added as needed to high shear system 100 via feed pump 4 and injection point 3.

As shown in FIG. 1, high shear system 100 may further comprise a cold trap. The cold trap may be used, for example, to take the recycle gases 17 into an ice cooler receiver from which the gas in line 25 is piped to compressor 50 to be injected into high shear device 40 via line 15.

Condenser 30 comprises an outlet line 24 for condensed product (e.g., hydrocarbons) and an outlet line 25 for a recycle gas stream. In embodiments, cold trap of condenser 30 serves to remove liquids from recycle line 17 upstream of recirculation pump or compressor 50. Recycle line 15 may be fluidly connected to line 13 for reintroduction of light gas to HSD 40, as shown in FIG. 1.

Temperature.

In some embodiments, use of any of the disclosed processes and/or systems includes reactant mixing via HSD 40 to permit conversion of gas and/or liquids to preferred hydrocarbonaceous products. The temperature within HSD 40 is desirably below the flash point of the liquid medium. In some embodiments, operating system or process conditions comprise a temperature in the range of from about 100° C. to about 230° C. In other embodiments, the temperature is in the range of about 115° C. to about 375° C., while in other embodiments, the temperature is in the range of from about 115° C. to 725° C. In some specific embodiments, the reaction temperature is in the range of from about 155° C. to about 160° C. The reaction temperature may be the localized temperature present within the HSD 40.

In embodiments, the product profile changes with temperature in vessel 10, and the reactor temperature may be adjusted to attain the desired product profile. At increased temperatures, a greater quantity of lower molecular weight materials may be produced, while, at lower temperatures, a greater quantity of higher molecular weight materials may be produced.

Pressure.

In any disclosed embodiments, the reaction pressure in vessel 10 may be in the range of from about 202.65 kPa (2 atm) to about 5.6 MPa-6.1 MPa (55-60 atm). In some embodiments, reaction pressure may in the range of from about 810.6 kPa to about 1.5 MPa (8 atm to about 15 atm). In embodiments, vessel 10 is operated at or near atmospheric pressure. In embodiments, reaction pressure is less than about 6895 kPa (1000 psi). Alternatively, in some embodiments, the operating pressure is less than about 3445 kPa (500 psi). In some embodiments, the operating pressure is less than about 3100 kPa (450 psi). In some embodiments, the operating pressure is less than about 1030 kPa (150 psi).

In some instances, it is desirable to further enhance the degree of product conversion. Increasing reaction pressure increases reaction rate, but also increases wear of the materials constituting the reactors, the piping, and the mechanical parts of the plant, as well as the ancillary devices. The superior dissolution and/or dispersion provided by the external high shear mixing may allow a decrease in operating pressure while maintaining or even increasing product production.

Catalyst.

A suitable catalyst may be used to promote reactions described herein, and the catalyst may be introduced as a slurry or catalyst stream into vessel 10, for example via line 3. Alternatively, or additionally, catalyst may be added elsewhere in system 100. For example, catalyst slurry may be injected into line 21. In some embodiments, system 100 comprises a closed slurry loop, and line 21 may contain liquid medium, liquid product, and/or catalyst recycled from line 16. In embodiments the catalyst may be a fixed bed catalyst.

As such, reactions may occur in the presence of a catalyst system which may comprise, for example, a Group VIII metallic element (e.g., Rh, Ir, Co, Ni, Ru, Pd or Pt). In an embodiment, the Group VIII element is Rh or Ir. In an embodiment, the catalyst comprises a halogen promoter, such as a hydrogen halide or organic halide, particularly an alkyl iodide such as methyl iodide, a stabilizer/copromoter, which is a salt of a metal of Group IA or IIA of the Periodic Table, or a quaternary ammonium or phosphosium salt, particularly an iodide or acetate salt and most often lithium iodide, or lithium acetate.

In an embodiment, the active portion of the catalyst is a complex of the Group VIII metal. In an embodiment, the active portion of the catalyst is added to the reaction section as a pre-formed complex rather than the described individual catalyst components. The catalyst system is dissolved or dispersed in a liquid medium comprising methyl acetate, acetic acid, a finite amount of water, e.g., at least about 0.1 wt. % and any other solvent component compatible with the other compounds present.

In an embodiment, the catalyst may include rhodium and rhodium/iridium metals and compounds as the Group VIII metal and an alkyl iodide as a halogen promoter. In an embodiment, a catalyst stabilizer/co-promoter is used as well. The stabilizer/co-promoter may be in the form of a soluble salt from an alkali metal or alkaline earth metal or a quaternary ammonium or phosphonium salt which generates an effective amount of iodide ion in the reaction solution. In an embodiment, the catalyst stabilizer/co-promoter is lithium iodide, lithium acetate or mixtures thereof. In an embodiment, the catalyst may include a transition metal salt as a co-promoter selected from the group consisting of salts of ruthenium, tungsten, osmium, nickel, cobalt, platinum, palladium, manganese, titanium, vanadium, copper, aluminum, tin, and antimony. Catalysts known to one skilled in the art are suitable for the process of this disclosure.

Figure 2:
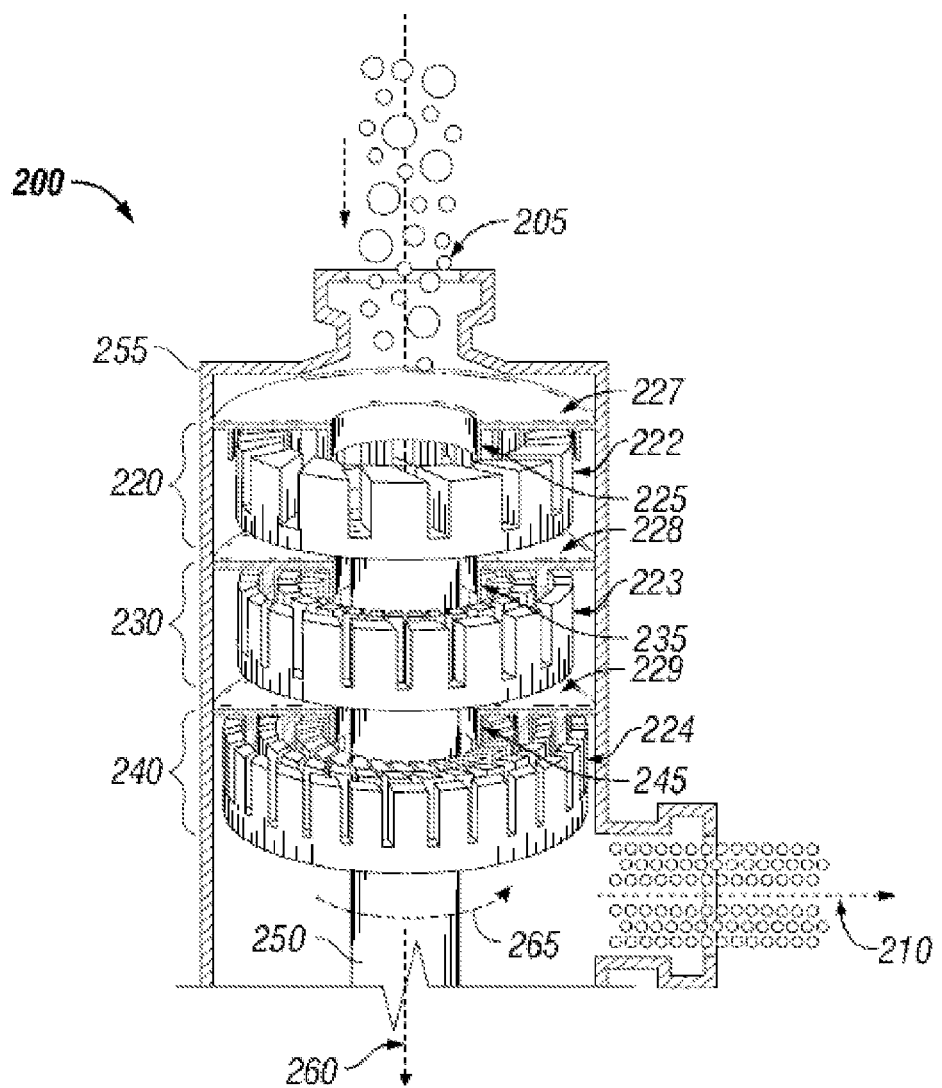
FIG. 2 is a longitudinal cross-section view of a multi-stage high shear device, as employed in embodiments of the system.

Referring now to FIG. 2, there is presented a longitudinal cross-section of a suitable high shear device 200. High shear device 200 of FIG. 2 is a dispersing device comprising three stages or rotor-stator combinations. High shear device 200 is a dispersing device comprising three stages or rotor-stator combinations, 220, 230, and 240. The rotor-stator combinations may be known as generators 220, 230, 240 or stages without limitation. Three rotor/stator sets or generators 220, 230, and 240 are aligned in series along drive shaft 250.

First generator 220 comprises rotor 222 and stator 227. Second generator 230 comprises rotor 223, and stator 228. Third generator 240 comprises rotor 224 and stator 229. For each generator the rotor is rotatably driven by input 250 and rotates about axis 260 as indicated by arrow 265. The direction of rotation may be opposite that shown by arrow 265 (e.g., clockwise or counterclockwise about axis of rotation 260). Stators 227, 228, and 229 are fixably coupled to the wall 255 of high shear device 200.

As mentioned hereinabove, each generator has a shear gap width which is the minimum distance between the rotor and the stator. In the embodiment of FIG. 2, first generator 220 comprises a first shear gap 225; second generator 230 comprises a second shear gap 235; and third generator 240 comprises a third shear gap 245. In embodiments, shear gaps 225, 235, 245 have widths in the range of from about 0.025 mm to about 10.0 mm. Alternatively, the process comprises utilization of a high shear device 200 wherein the gaps 225, 235, 245 have a width in the range of from about 0.5 mm to about 2.5 mm. In certain instances the shear gap width is maintained at about 1.5 mm. Alternatively, the width of shear gaps 225, 235, 245 are different for generators 220, 230, 240. In certain instances, the width of shear gap 225 of first generator 220 is greater than the width of shear gap 235 of second generator 230, which is in turn greater than the width of shear gap 245 of third generator 240. As mentioned above, the generators of each stage may be interchangeable, offering flexibility. High shear device 200 may be configured so that the shear rate will increase stepwise longitudinally along the direction of the flow 260.

Generators 220, 230, and 240 may comprise a coarse, medium, fine, and super-fine characterization. Rotors 222, 223, and 224 and stators 227, 228, and 229 may be toothed designs. Each generator may comprise two or more sets of rotor-stator teeth. In embodiments, rotors 222, 223, and 224 comprise more than 10 rotor teeth circumferentially spaced about the circumference of each rotor. In embodiments, stators 227, 228, and 229 comprise more than ten stator teeth circumferentially spaced about the circumference of each stator. In embodiments, the inner diameter of the rotor is about 12 cm. In embodiments, the diameter of the rotor is about 6 cm. In embodiments, the outer diameter of the stator is about 15 cm. In embodiments, the diameter of the stator is about 6.4 cm. In some embodiments the rotors are 60 mm and the stators are 64 mm in diameter, providing a clearance of about 4 mm. In certain embodiments, each of three stages is operated with a super-fine generator, comprising a shear gap of between about 0.025 mm and about 4 mm. For applications in which solid particles are to be sent through high shear device 40, the appropriate shear gap width (minimum clearance between rotor and stator) may be selected for an appropriate reduction in particle size and increase in particle surface area. In embodiments, this may be beneficial for increasing surface area of solid catalyst by shearing and dispersing the particles.

High shear device 200 is configured for receiving from line 13 a reaction mixture at inlet 205. The reaction mixture may comprise gas as the dispersible phase and liquid medium as the continuous phase. The feed stream may further comprise a particulate solid catalyst component. Feed stream entering inlet 205 is pumped serially through generators 220, 230, and then 240, such that a dispersion is formed. The dispersion exits high shear device 200 via outlet 210 (and line 18 of FIG. 1). The rotors 222, 223, 224 of each generator rotate at high speed relative to the fixed stators 227, 228, 229, providing a high shear rate. The rotation of the rotors pumps fluid, such as the feed stream entering inlet 205, outwardly through the shear gaps (and, if present, through the spaces between the rotor teeth and the spaces between the stator teeth), creating a localized high shear condition. High shear forces exerted on fluid in shear gaps 225, 235, and 245 (and, when present, in the gaps between the rotor teeth and the stator teeth) through which fluid flows process the fluid and create the dispersion. The product dispersion exits high shear device 200 via high shear outlet 210 (and line 18 of FIG. 1).

The produced dispersion has an average gas bubble size less than about 5 μm. In embodiments, HSD 40 produces a dispersion having a mean bubble size of less than about 1.5 size is from about 0.1 μm to about 1.0 μm. In embodiments, HSD 40 produces a dispersion having a mean bubble size of less than 400 nm. In embodiments, HSD 40 produces a dispersion having a mean bubble size of less than 100 nm. High shear device 200 produces a dispersion comprising dispersed gas bubbles capable of remaining dispersed at atmospheric pressure for at least about 15 minutes. In embodiments, the exit stream from HSD 40 includes the dispersion and/or products formed in the HSD 40.

Not to be limited by theory, it is known in emulsion chemistry that sub-micron particles, or bubbles, dispersed in a liquid undergo movement primarily through Brownian motion effects. The bubbles in the product dispersion created by high shear device 200 may have greater mobility through boundary layers of solid catalyst particles (if present), thereby further facilitating and accelerating the conversion reaction through enhanced transport of reactants in a heterogeneous reaction mixture.

In certain instances, high shear device 200 comprises a Dispax Reactor® of IKA® Works, Inc. Wilmington, N.C. and APV North America, Inc. Wilmington, Mass. Several models are available having various inlet/outlet connections, horsepower, tip speeds, output rpm, and flow rate. Selection of the high shear device will depend on throughput requirements and desired particle or bubble size in dispersion in line 18 (FIG. 1) exiting outlet 210 of high shear device 200. IKA® model DR 2000/4, for example, comprises a belt drive, 4M generator, PTFE sealing ring, inlet flange 25.4 mm (1 inch) sanitary clamp, outlet flange 19 mm (¾ inch) sanitary clamp, 2HP power, output speed of 7900 rpm, flow capacity (water) approximately 300-700 L/h (depending on generator), a tip speed of from 9.4-41 m/s (1850 ft/min to 8070 ft/min).

Conversion of a Carbon-Based Component and a Hydrogen-Based Component.

In an embodiment, methods disclosed herein may include reacting, for example, CO (or CH2) and CH4 in a liquid medium to form a product stream that includes the steps of feeding CO and CH4 to an HSD (40, FIG. 1); using the HSD to form the dispersion comprising CO and CH4; providing the dispersion into a reactor or vessel (10, FIG. 1); and reacting the dispersion in the reactor to produce the product stream comprising the desired organic products. For example, the product stream may comprise alkanes, olefins, aromatics, and combinations thereof.

Operation of high shear system 100 will now be discussed with reference again to FIG. 1. In embodiments, system 100 may include one or more dispersible gas streams. For example, high shear system 100 may include dispersible gas line 22 and dispersible gas line 23. In operation for the conversion of a carbon-based reactant to an organic product, a dispersible light gas stream may be introduced into system 100 via line 22 and/or line 23, and combined in line 13 with a liquid stream or medium. In an embodiment, the liquid medium is a solvent. In an embodiment, the liquid medium is a Fischer-Tropsch liquid.

Dispersible gas in line 22 and/or line 23, compressed recycle fluid in line 15 and liquid medium in line 21 may be introduced separately or as a mixed stream into external high shear device 40. As shown in FIG. 1, in embodiments, dispersible gas stream in line 22 and/or line 23 may be introduced into liquid medium and the combined gas/liquid (or gas/liquid/solid or liquid/liquid) stream is introduced into HSD 40.

Dispersible gas introduced into HSD 40 may thus comprise a light gas. The light gas to be dispersed in HSD 40 may be a mixture of CH4 and a carbon-based component, such as, for example, CO or CO2. As sources of natural gas often comprise additional gaseous components, the light gas introduced into line 13 via line 22, and/or line 23 may further comprise up to about 10% of additional gaseous components. The additional gaseous components may be, for example, ethane, propane, butane, pentane, methanol or a combination thereof. In some embodiments, light gas comprises methane, ethane, propane, butane, or a combination thereof, and light gas in line 23 comprises CO.

In some embodiments, the dispersible gas may comprise CH4, while in other embodiments the dispersible gas may comprise CO. In yet other embodiments, light gas may comprise CO and CH4. Light gas may be continuously fed into line 13.

In some embodiments, light gas comprises CH4. In embodiments, dispersible light gas comprises CO2. In embodiments, light gas may include a CO2 and CH4 mixture. In embodiments, light gas comprises a 2:1 ratio of methane to carbon dioxide. In embodiments, the light gas comprises carbon dioxide, hydrogen, and carbon monoxide. In embodiments, light gas is continuously fed into line 13. In embodiments, the feed rate of dispersible light gas is greater than about 50 cc/min. Alternatively, the feed rate of dispersible light gas is greater than about 80 cc/min. Alternatively, the feed rate of dispersible light gas is greater than about 2300 cc/min. In an embodiment, the feed stream may be a liquid or gas phase. In a further embodiment, the feed may include up to 25% CO2 and up to 25% CH4 (volumetric basis).

In yet other embodiments, the dispersible gas may include H2 and CO. The H2:CO ratio of the dispersible synthesis gas stream introduced via line 22 may be from about 1:1 to about 5:1. In embodiments, the H2:CO ratio of the dispersible synthesis gas stream introduced via line 22 may be from about 1.7:1 to about 3:1. In embodiments, the H2:CO ratio may be about 2. Typically, synthesis gas is produced via gas reformation or gasification of solids, depending on the raw material or feedstock available. In embodiments, H2 and CO in dispersible line 22 may be synthesis gas produced via reforming or partial oxidation of natural gas. In embodiments, synthesis gas in line 22 may be obtained via gasification of a solid material such as, but not limited to, coal, biomass, and biorenewables.

Although various examples are provided, the feed rate and/or the feed streams fed to the system may be varied as necessary in order to, for example, obtain the desired products.

In embodiments, the liquid medium and a suitable catalyst may be mixed prior to introduction into vessel 10. For example, a FT liquid and catalyst (if used) may be initially charged into vessel 10 prior to sealing units. In embodiments, catalyst is added to liquid medium in a stirred beaker. In other embodiments, the liquid medium and catalyst are introduced separately and then mixed within vessel 10 via reactor agitator 31. Additional reactants may be added to vessel 10 if desired for a particular application, for example via feed pump 4 and inlet line 3. Any number of vessel 10 inlet lines may be utilized. High shear system 100 may then be sealed and vessel 10 evacuated. In embodiments, vessel 10 is purged with nitrogen. In embodiments, vessel 10 is purged with oxygen. For example, a vacuum may be pulled via reactor gas line 17.

Dispersible light gas may be injected into high shear system 100 until the pressure in vessel 10 reaches a desired range. In embodiments, dispersible light gas is introduced into high shear device 40 until a pressure of 206.8 kPa (30 psi) is attained in vessel 10. Next, high shear device 40 may be placed in operation, reactor agitation via, for example, stirring system 31 continued, and high shear pumping of reactor fluids throughout high shear system 100 commenced. In some embodiments, the system is a closed loop with no venting at this point.

In embodiments, dispersible light gas(es) or other liquids may be fed directly into HSD 40, instead of being combined with the liquid medium in line 13. Pump 5 may be operated to pump the liquid medium through line 21, and to build pressure and feed HSD 40, providing a controlled flow throughout high shear device (HSD) 40 and high shear system 100. In some embodiments, pump 5 increases the pressure of the HSD inlet stream to greater than 202.65 kPa (2 atm), alternatively greater than about 303.975 kPa (3 atmospheres). In this way, high shear system 100 may combine high shear with pressure to enhance reactant intimate mixing.

Via pumping, the light gas and liquid medium are mixed within HSD 40, which serves to create a fine dispersion of the light gas in the liquid medium, such that at least one liquid phase reactant is formed. In HSD 40, the light gas and liquid medium are highly dispersed such that nanobubbles, submicron-sized bubbles, and/or microbubbles of the light gas are formed for superior dissolution into solution and enhancement of reactant mixing. For example, disperser IKA® model DR 2000/4, a high shear, three stage dispersing device configured with three rotors in combination with stators, aligned in series, may be used to create the dispersion of dispersible light gas in liquid medium. The rotor/stator sets may be configured as illustrated in FIG. 2, for example. The combined reactants enter the high shear device via line 13 and enter a first stage rotor/stator combination.

The rotors and stators of the first stage may have circumferentially spaced first stage rotor teeth and stator teeth, respectively. The coarse dispersion exiting the first stage enters the second rotor/stator stage. The rotor and stator of the second stage may also comprise circumferentially spaced rotor teeth and stator teeth, respectively. The reduced bubble-size dispersion emerging from the second stage enters the third stage rotor/stator combination, which may comprise a rotor and a stator having rotor teeth and stator teeth, respectively. The dispersion exits the high shear device via line 18.

In some embodiments, the shear rate increases stepwise longitudinally along the direction of the flow, 260. For example, in some embodiments, the shear rate in the first rotor/stator stage is greater than the shear rate in subsequent stage(s). In other embodiments, the shear rate is substantially constant along the direction of the flow, with the shear rate in each stage being substantially the same.

The rotor(s) of HSD 40 may be set to rotate at a speed commensurate with the diameter of the rotor and the desired tip speed. As described above, the high shear device (e.g., colloid mill or toothed rim disperser) has either a fixed clearance between the stator and rotor or has adjustable clearance. In some embodiments of the process, the transport resistance of the reactants is reduced by operation of the high shear device such that the rate of the reaction is increased by greater than about 5%. In some embodiments of the process, the transport resistance of the reactants is reduced by operation of the high shear device such that the rate of the reaction is increased by greater than a factor of about 5. In some embodiments, the rate of the reaction is increased by at least a factor of 10. In some embodiments, the rate is increased by a factor in the range of about 10 to about 100 fold.

In some embodiments, HSD 40 delivers at least 300 L/h at a tip speed of at least 4500 ft/min, and which may exceed 7900 ft/min (40 m/s). The power consumption may be about 1.5 kW.

In embodiments, the temperature in HSD 40 may be in the range of at least about 125° C. The temperature may be a localized temperature present in a shear gap or at the tip of a rotor, and may be suitable to promote reaction of the HSD 40 contents.

Although measurement of instantaneous temperature and pressure at the tip of a rotating shear unit or revolving element in HSD 40 may be difficult, it is estimated that the localized temperature seen by the intimately mixed reactants may be in excess of 500° C. and at pressures in excess of 500 kg/cm$^2$ under cavitation conditions. The high shear mixing results in dispersion of the light gas in micron or submicron-sized bubbles. In some embodiments, the resultant dispersion has an average bubble size less than about 1.5 μm. Accordingly, the dispersion exiting HSD 40 via line 18 comprises micron and/or submicron-sized gas bubbles. In some embodiments, the mean bubble size is in the range of about 0.4 μm to about 1.5 μm. In some embodiments, the resultant dispersion has an average bubble size less than 1 μm. In some embodiments, the mean bubble size is less than about 400 nm, and may be about 100 nm in some cases. In many embodiments, the dispersion is able to remain dispersed at atmospheric pressure for at least 15 minutes. In some embodiments, the average bubble size refers to the average bubble diameter under reaction conditions.

Once dispersed, the resulting gas/liquid (or optionally gas/liquid/solid, liquid/liquid, etc.) dispersion exits HSD 40 via line 18 and feeds into vessel 10, as illustrated in FIG. 1. Dispersion in line 18 may optionally undergo further processing (heating/cooling) as may be desired in a particular application prior to entering vessel 10. As a result of the intimate mixing of the reactants prior to entering vessel 10, a significant portion of the chemical reaction may take place in HSD 40. Accordingly, in some embodiments, reactor/vessel 10 may be used primarily for heating and separation of product liquids from unreacted light gas and any product gas. Alternatively, or additionally, vessel 10 may serve as a primary reaction vessel where most of the organic product is produced. For example, in embodiments, vessel 10 is a fixed bed reactor comprising a fixed bed of catalyst.

If a catalyst is used to promote the conversion reactions, the catalyst may be introduced as a slurry or catalyst stream into vessel 10, for example via line 3. Alternatively, or additionally, catalyst may be added elsewhere in system 100. For example, catalyst slurry may be injected into line 21. In some embodiments, system 100 comprises a closed slurry loop, and line 21 may contain liquid medium, liquid product, and/or catalyst recycled from line 16. In embodiments the catalyst may be a fixed bed catalyst.

Vessel/reactor 10 may be operated in either continuous or semi-continuous flow mode, or it may be operated in batch mode. The contents of vessel 10 may be maintained at a specified reaction temperature using heating and/or cooling capabilities (e.g., heater H1) and temperature measurement instrumentation. Pressure in the vessel may be monitored using suitable pressure measurement instrumentation, and the level of reactants in the vessel may be controlled using a level regulator (not shown), employing techniques that are known to those of skill in the art. The contents may be stirred continuously or semi-continuously with, for example stirring system 31.

In embodiments, at least a portion of the reaction mixture in line 16 comprising liquid medium, liquid product, and optional catalyst is recirculated to HSD 40 for multi-pass operation. Line 16 may be fluidly connected to line 21 by line 20, for recycle of at least a portion of line 16 to HSD 40. As shown in FIG. 1, heat transfer device H2 may serve to control the temperature of line 21.

Unreacted light gas along with any other gas in vessel 10 may exit vessel 10 via gas line 17. As shown in FIG. 1, in embodiments, gas recovered from the vessel 10 headspace may be passed through a condenser 30. Extraction of reactor gas from vessel 10 may be aided by, for example, compressor 50. Condenser 30 may comprise a cooling coil and cold trap. Non condensed gases from condenser 30 may be introduced via line 25 to a compressor 50. Compressed gas may be recycled via, for example, line 15. Line 15 may introduce compressed material from compressor 50 injected into HSD 40, independently, or into line 13, line 22, and/or line 23. Condensed liquid product 24 exiting condenser 30 is extracted from the system. Condensed liquid in line 24 comprises reaction products that may be utilized by any means known in the art, for example sale thereof or conversion into various other chemical products.

According to this disclosure, at least one surface within HSD 40 may be made of, impregnated with, or coated with a catalyst suitable for catalyzing a desired reaction. For example, in embodiments, all or a portion of at least one rotor, at least one stator, or at least one rotor/stator set (i.e., at least one generator) is made of, coated with, or impregnated with a suitable catalyst. In some applications, it may be desirable to utilize two or more different catalysts. In such instances, a generator may comprise a rotor made of, impregnated with, or coated with a first catalyst material, and the corresponding stator of the generator may be made of, coated with, or impregnated by a second catalyst material. Alternatively one or more rings of the rotor may be made from, coated with, or impregnated with a first catalyst, and one or more rings of the rotor may be made from, coated with, or impregnated by a second catalyst. Alternatively one or more rings of the stator may be made from, coated with, or impregnated with a first catalyst, and one or more rings of the stator may be made from, coated with, or impregnated by a second catalyst. All or a portion of a contact surface of a stator, rotor, or both can be made from or coated with catalytic material.

By contacting the reactants with the rotating members, which can be made from, coated with, or impregnated with stationary catalyst, significant energy is transferred to the reaction. Especially in instances where the reactants are gaseous, the energy consumption of the HSD 40 will be very low. The temperature may be adjusted to control the product profile and to extend catalyst life.

Methanol Carbonylation.

Operation of high shear system 100 for the production of acetic acid will now be discussed with reference again to FIG. 1. It is noted that various features, functions, operable parameters, etc. described previously are applicable to the description as follows, and are not repeated verbatim in order to simplify additional aspects to the reader. A process for the production of acetic acid may occur by carbonylation of an alkyl alcohol, such as methanol (and reactive derivatives thereof), an ether, such as dimethyl ether, an oxide, such as ethylene oxide, or other suitable compounds subject to reaction with carbon monoxide in a liquid medium. These reactions (for example, see below) may be carried out in the presence of a catalyst, such as rhodium and iridium, or any other catalyst suitable to the reaction conditions.

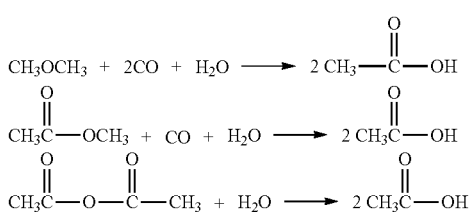

In accordance with embodiments disclosed herein, system 100 may include two or more streams (e.g., 13, 22, 23) fed, directly or indirectly, to HSD 40. In operation, a feed stream may be introduced into system 100 via line 22 and/or line 23, and combined in line 13 with a liquid medium. The feed mixture in line 13 may comprise one or more of hydrogen, methane, CO, CO2, water, another inert gas or hydrocarbon reactant. In an embodiment, a stream of a first reactant, such as an alkyl alcohol, and a second reactant, such as CO, may be fed through any of lines 13, 22, 23, and into HSD 40, where a highly sheared dispersion may be formed, and reacted. In an embodiment, the dispersion may react, in some instances instantaneously, within the HSD 40. The dispersion may also be feed continuously, or as desired, to a reactor vessel 10 where the carbonylation reaction may also occur. The carbonylation process may occur with the catalyst (e.g., Group VIII metal) dissolved or disposed in the liquid medium through which gas, such as CO, may also be bubbled therethrough.

Unreacted light gas along with any other gas in vessel 10 may exit vessel 10 via gas line 17. As shown in FIG. 1, in embodiments, lights recovered from the vessel 10 headspace may be passed through a condenser 30. Extraction of reactor gas from vessel 10 may be aided by, for example, compressor 50. Condenser 30 may comprise a cooling coil and cold trap. Non condensed gases from condenser 30 may be introduced via line 25 to a compressor 50. Compressed gas may be recycled via, for example, line 15. Line 15 may introduce compressed material from compressor 50 injected into HSD 40, independently, or into line 13, line 22, and/or line 23. Condensed liquid product 24 exiting condenser 30 is extracted from the system. Condensed liquid in line 24 comprises reaction products that may be utilized by any means known in the art, for example sale thereof or conversion into various other chemical products.

Dispersible gas in line 22 and/or line 23, compressed recycle fluid in line 15 and liquid medium in line 21 are introduced separately or as a mixed stream into external high shear device 40. As shown in FIG. 1, in embodiments, dispersible gas stream in line 22 and/or line 23 is introduced into liquid medium (which may comprise hydrogen source or hydrogen source and catalyst) and the combined gas/liquid (or gas/liquid/solid or liquid/liquid) stream is introduced into HSD 40.

As mentioned, dispersible gas introduced into HSD 40 may be a light gas. The light gas to be dispersed in HSD 40 may be, for example, CH4, CO, or a combination thereof. In some embodiments, the dispersible gas may comprise CH4, while in other embodiments the dispersible gas may comprise CO. In yet other embodiments, light gas may comprise CO and CH4. Light gas may be continuously fed into line 13.

The feed rate and/or the feed streams fed to the system may be varied as necessary in order to, for example, obtain the desired products, as would be apparent to one of skill in the art.

The liquid medium may be a variety of types, such as a hydrocarbon, water, etc., or another solvent compatible with the process components, may also be used. As such, the liquid medium in line 21 may comprise at least one hydrogen source. In embodiments, liquid medium is selected from water, lower molecular weight liquid alkanes, paraffinic oils and combinations thereof. In embodiments, the liquid medium and a suitable catalyst may be mixed prior to introduction into vessel 10. In embodiments, catalyst is added to liquid medium in a stirred beaker. In other embodiments, the liquid medium and catalyst are introduced separately and mixed within HSD 40. In yet other embodiments, the liquid medium and catalyst are introduced separately and mixed within vessel 10 via reactor agitator 31.

Pump 5 may be operated to pump the liquid medium through line 21, and to build pressure and feed HSD 40, providing a controlled flow throughout high shear device (HSD) 40 and high shear system 100. In some embodiments, pump 5 increases the pressure of the HSD inlet stream to greater than 202.65 kPa (2 atm), alternatively greater than about 303.975 kPa (3 atmospheres). In this way, high shear system 100 may combine high shear with pressure to enhance reactant intimate mixing.

After pumping, the light gas and liquid medium are mixed within HSD 40, which serves to create a fine dispersion of the light gas in the liquid medium. In HSD 40, the light gas and liquid medium are highly dispersed such that nanobubbles, submicron-sized bubbles, and/or microbubbles of the light gas are formed for superior dissolution into solution and enhancement of reactant mixing.

In embodiments, at least a portion of the reaction mixture in line 16 comprising liquid medium, liquid product, and optional catalyst is recirculated to HSD 40 for multi-pass operation. Line 16 may be fluidly connected to line 21 by line 20, for recycle of at least a portion of line 16 to HSD 40. As shown in FIG. 1, heat transfer device H2 may serve to control the temperature of line 21.

Conversion of Acetic Acid.

Operation of high shear system 100 for the production of ethanol by the hydrogenation of acetic acid (see below) will now be discussed with reference again to FIG. 1.

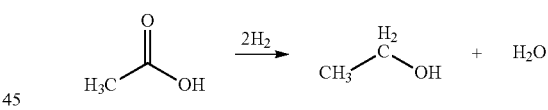

It is noted that various features, functions, operable parameters, etc. described previously are applicable to the description as follows, and are not repeated verbatim in order to simplify additional aspects to the reader. Embodiments disclosed herein may relate to the production of ethanol from acetic acid, and more specifically, to a process that includes hydrogenation of acetic acid (with or without a catalyst) to form ethanol with high conversion and selectivity.

The raw materials used in connection with the process of embodiments described may be derived from any suitable source including natural gas, petroleum, coal, biomass and so forth. Advantageously acetic acid may be produced through methanol carbonylation process according to embodiments disclosed herein and as previously described.

In accordance with the disclosure, system 100 may include two or more streams 13, 22, 23 fed, directly or indirectly, to HSD 40. In operation for the production of ethanol, a feed stream may be introduced into system 100 via line 22 and/or line 23, and combined in line 13 with a liquid medium. Thus, the feed mixture in line 13 may include acetic acid and/or another liquid. In an embodiment, a stream of a first reactant, such as hydrogen, and a second reactant, such as acetic acid, may be fed through lines 22 and 23, and into HSD 40, where in the presence of the liquid medium a highly sheared dispersion may be formed. The liquid medium may be a hydrocarbon, water, etc., or another solvent compatible with the process components. If a catalyst is used, various hydrogenating catalysts known to one skilled in the art are readily usable with the process.

Dispersible gas in line 22 and/or line 23, compressed recycle fluid in line 15 and liquid medium in line 21 may be introduced separately or as a mixed stream into external high shear device 40. As shown in FIG. 1, streams in line 22 and/or line 23 may be introduced into liquid medium (which may comprise hydrogen source or hydrogen source and catalyst) and the combined streams (e.g., gas/liquid, gas/liquid/solid, liquid/liquid) may be introduced into HSD 40.

The dispersible gas introduced into HSD 40 may be a light gas, which may be hydrogen or other suitable hydrogen donor. Light gas may be continuously fed into line 13. The feed rate and/or the feed streams fed to the system may be varied as necessary in order to, for example, obtain the desired products, as would be apparent to one of skill in the art.

The liquid medium may be a variety of types. The liquid medium in line 21 may comprise at least one hydrogen source, which may, for example, be selected from water, hydrocarbons, and combinations thereof. In embodiments, liquid medium is selected from water, lower molecular weight liquid alkanes, paraffinic oils and combinations thereof. Thus, the liquid medium may include CH4. The paraffinic oil may be either hydroprocessed petroleum derived oil, such as the Paralux oils as supplied by Chevron Products Company or synthetic paraffin oils. Suitable synthetic paraffinic oils include, for example, poly-alpha olefins (API) Group IV base oil as well as hydrocracked/hydroisomerized (API) Group III base oils. Such Group (IV) base oil includes oil such as a low weight component of Polyethylene-propylene.

The rotor(s) of HSD 40 may be set to rotate at a speed commensurate with the diameter of the rotor and the desired tip speed. As described above, the high shear device (e.g., colloid mill or toothed rim disperser) has either a fixed clearance between the stator and rotor or has adjustable clearance. In some embodiments of the process, the transport resistance of the reactants is reduced by operation of the high shear device such that the rate of the reaction is increased by greater than about 5%. In some embodiments of the process, the transport resistance of the reactants is reduced by operation of the high shear device such that the rate of the reaction is increased by greater than a factor of about 5. In some embodiments, the rate of the reaction is increased by at least a factor of 10. In some embodiments, the rate is increased by a factor in the range of about 10 to about 100 fold.

Once dispersed, the resulting dispersion (e.g., gas/liquid, gas/liquid/solid, liquid/liquid, etc.) may instantaneously react in the HSD 40 as a result of localized conditions being favorable to reaction. The dispersion and/or products may also exit HSD 40 via line 18 and feed into vessel 10, as illustrated in FIG. 1. Dispersion in line 18 may optionally undergo further processing (heating/cooling) as may be desired in a particular application prior to entering vessel 10. As a result of the intimate mixing of the reactants prior to entering vessel 10, a significant portion of the chemical reaction may take place in HSD 40. Accordingly, in some embodiments, reactor/vessel 10 may be used primarily for heating and separation of product liquids from unreacted light gas and any product gas. Alternatively, or additionally, vessel 10 may serve as a primary reaction vessel where most of the organic product is produced. For example, in embodiments, vessel 10 is a fixed bed reactor comprising a fixed bed of catalyst.

In some instances, it is desirable to further enhance the degree of product conversion. Increasing reaction pressure increases reaction rate, but also increases wear of the materials constituting the reactors, the piping, and the mechanical parts of the plant, as well as the ancillary devices. The superior dissolution and/or dispersion provided by the external high shear mixing may allow a decrease in operating pressure while maintaining or even increasing product production.

Multiple Pass Operation.

As shown in FIG. 1, it may be desirable to pass the contents of vessel 10, or a fraction thereof, through HSD 40 during a second pass. In this case, line 16 may be connected to line 21 as indicated, such that at least a portion of the contents of line 16 is recycled from vessel 10 and pumped by pump 5 into line 13 and thence into HSD 40. Additional light gas may be injected into line 13, or may be added directly into the high shear device (not shown). In other embodiments, product in line 16 may be further treated into, for example, a separation device usable to remove liquid product therefrom, prior to recycle of a portion of the liquid in line 16 to high shear device 40. In some embodiments it may be desirable to pass the liquid medium and dispersible gas through high shear device 40 and then add optional catalyst into line 13 during a second pass through HSD 40.

Multiple High Shear Mixing Devices.

In some embodiments, two or more high shear devices like HSD 40, or configured differently, are aligned in series, and are used to further enhance the reaction. Their operation may be in either batch or continuous mode. In some instances in which a single pass or "once through" process is desired, the use of multiple high shear devices in series may be advantageous. For example, in embodiments, outlet dispersion in line 18 may be fed into a second high shear device. When multiple high shear devices 40 are operated in series, additional light gas may be injected into the inlet feedstream of each device. In embodiments where multiple high shear devices 40 are operated in series, vessel 10 may be omitted. In some embodiments, multiple high shear devices 40 are operated in parallel, and the outlet dispersions therefrom are introduced into one or more vessel 10.

Product/Downstream Processing.

Gas is removed from vessel 10 via gas outlet line 17. The gas in line 17 may comprise unreacted ingredients, light gases, and/or hydrocarbon product. Gas removed via reactor gas outlet 17 may be further treated and its components recycled. For example, condenser 30 may be used to condense and remove from gas line 17 any product hydrocarbons that escapes vessel 10 in recycle gas line 17.

A portion of product in line 16 may be removed from vessel 10. Organic product in line 16 may include C2+ hydrocarbons, as well as liquid reactants. The product stream may comprise primarily hydrocarbons produced during reaction along with liquid medium. In some embodiments, the product in line 16 may include C5+ hydrocarbons. The liquid product recovered from product line 16 and/or condensate line 24 may then be used as a fuel or utilized as a feed stock to another chemical processes, as known to those of skill in the art.

Features.

The increased surface area of the micrometer sized and/or submicrometer sized light gas bubbles in the dispersion in line 18 produced within high shear device 40 results in faster and/or more complete conversion of light gas. As mentioned hereinabove, additional benefits are the ability to operate vessel 10 at lower temperatures and pressures resulting in both operating and capital cost savings. The benefits of the present disclosure include, but are not limited to, faster cycle times, increased throughput, reduced operating costs and/or reduced capital expense due to the possibility of designing smaller reactors, and/or operating the reactor at lower temperature and/or pressure and the possible reduction in catalyst.

The application of enhanced mixing of the reactants by HSD 40 potentially permits significant production of organic product from light gas. In some embodiments, the enhanced mixing potentiates an increase in throughput of the process stream. In some embodiments, the high shear mixing device is incorporated into an established process, thereby enabling an increase in production (i.e., greater throughput). In contrast to some methods that attempt to increase the degree of conversion by simply increasing reactor pressures, the superior dispersion and contact provided by external high shear mixing may allow in many cases a decrease in overall operating pressure while maintaining or even increasing product production.

The hydrocarbon or organic product produced via the high shear system and process may comprise a mixture of hydrocarbons having a chain length of greater than 5 carbon atoms. The hydrocarbon product may comprise a mixture of hydrocarbons having chain lengths from 5 to about 90 carbon atoms. In embodiments, the majority of the hydrocarbons in the hydrocarbon product have a chain length in the range of from 5 to about 30 carbon atoms. Product upgrading may produce a wide range of commercial products, for example, gasoline, candle wax, and middle distillate fuels including diesel, naphtha, and kerosene.

Without wishing to be limited to a particular theory, it is believed that the level or degree of high shear mixing is sufficient to increase rates of mass transfer and also produces localized non-ideal conditions that permit reactions to occur that would not otherwise be expected to occur based on Gibbs free energy predictions. Localized non ideal conditions are believed to occur within the high shear device resulting in increased temperatures and pressures with the most significant increase believed to be in localized pressures. These conditions may advantageously promote reactions disclosed herein that normally would not be favorable to occur. The increase in pressures and temperatures within the high shear device are instantaneous and localized and quickly revert back to bulk or average system conditions once exiting the high shear device.

The temperature and pressure may be related to the capabilities of the shear device. The reactions described herein may advantageously occur under the higher temperature/pressure conditions experienced in the very localized area of the rotor/stator shear gap, where cavitation conditions may also exist.

In some cases, the high shear mixing device induces cavitation of sufficient intensity to dissociate one or more of the reactants into free radicals, which may intensify a chemical reaction or allow a reaction to take place at less stringent conditions than might otherwise be required. Cavitation may also increase rates of transport processes by producing local turbulence and liquid micro-circulation (acoustic streaming). An overview of the application of cavitation phenomenon in chemical/physical processing applications is provided by Gogate et al., "Cavitation: A technology on the horizon," *Current Science* 91 (No. 1): 35-46 (2006).

In some embodiments, the system and methods described herein permit design of a smaller and/or less capital intensive process than previously possible without the use of external high shear device 40. Potential advantages of certain embodiments of the disclosed methods are reduced operating costs and increased production from an existing process.

An approximation of energy input into the fluid (kW/L/min) can be estimated by measuring the motor energy (kW) and fluid output (L/min). As mentioned above, tip speed is the velocity (ft/min or m/s) associated with the end of the one or more revolving elements that is creating the mechanical force applied to the fluid. In embodiments, the energy expenditure is at least about 1000 W/m³. The actual energy input needed is a function of what reactions are occurring within the HSD, for example, endothermic and/or exothermic reaction(s), as well as the mechanical energy required for dispersing and mixing feedstock materials. In some applications, the presence of exothermic reaction(s) occurring within the HSD mitigates some or substantially all of the reaction energy needed from the motor input. When dispersing a gas in a liquid, the energy requirements are significantly less.

Without wishing to be limited to a particular theory, it is believed that the HSD of certain embodiments of the present system and methods may induce cavitation whereby one or more reactant is dissociated into free radicals, which then react. In embodiments, the extreme pressure at the tips of the rotors/stators leads to liquid phase reaction, and no cavitation is involved.

EXAMPLES

Various dimensions, sizes, quantities, volumes, rates, and other numerical parameters and numbers have been used for purposes of illustration and exemplification of the principles of embodiments described herein, and are not intended to limit any particular embodiment to the numerical parameters and numbers illustrated, described or otherwise stated herein. Likewise, unless specifically stated, the order of steps is not considered critical. The different teachings of the embodiments discussed below may be employed separately or in any suitable combination to produce desired results.

Probable reactions of CO with CH4 would normally be gas phase reactions; however, there are known solvents that CO and CH4 can be dissolved/dispersed in. Unfortunately, it is very difficult to find solvents that are liquid at high temperatures. Therefore, any reactions in a solvent are performed at temperatures less than 300° C. Pressures may be used to keep the solvent in the liquid phases, as well as to increase the solubility of CH4 and CO.

In accordance with embodiments disclosed herein it has been determined that with high shear the normal equilibrium calculations, which are based on no external work or forces, must be modified. With the use of high shear, unfavorable reactions may become feasible. For example, reactions of CH4 and CO suitable to produce alkanes, olefins, and/or aromatics appear to be in the temperature range of interest, which is from about 125° C. to about 325° C. However, typical reactions that one might write to produce these products would be unfavorable based on classical thermodynamics. However, in the system with high shear, high external forces are generated which can make such reactions favorable. Examples of reactions that are thermodynamically unfavorable under classical thermodynamic analyses include:

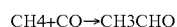

CH4+CO→CH3CHO

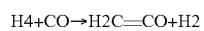

H4+CO→H2C=CO+H2

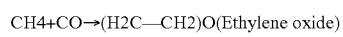

CH4+CO→(H2C—CH2)O(Ethylene oxide)

In the temperature range described, these reactions are unfavorable with classical thermodynamics. But by creating high local temperatures, in conjunction with high shear, the reactions may be favored in local areas of extreme conditions of temperature, pressure, and fluid shear. An unfavorable reaction is one for which the net Gibbs free energy is positive.

Possible representation of the effect of external mechanical (high shear) effects on reaction equilibrium is as follows:

$$-RT \log_e K_{equil}^{\circ}.$$

other effects, and X=a vector representing displacement distance.

Comparative 1

Potential Reactions of methane and CO and or CO2 [conventionally unfavorable with liquid(s) phase at temperatures of 125° C. to about 725° C.], including as a comparative example:

$$CH4+CO \Leftrightarrow CH_3CHO \text{(acetaldehyde)}$$

In accordance with the disclosure, a method of reacting methane and carbon monoxide to form an organic product, such as acetaldehyde, may be accomplished by feeding liquid methane to a high shear device, the high shear device comprising a shear gap; feeding a carbon monoxide gas to the high shear device; using the high shear device to form a dispersion comprising carbon monoxide gas and the methane liquid medium, wherein the dispersion comprises carbon monoxide Local conditions within the high shear device may result in reacting the dispersion to produce the organic product. Local conditions may include a local pressure of at least about 1034.2 MPa (150,000 psi) at the tip of a first rotor disposed therein. Local conditions may include a temperature in the range of about 125° C. to about 325° C. in the high shear device (e.g., at a rotor tip). Local conditions may include a temperature at a tip of the first rotor of at least 400° C.

The use of the local reaction conditions obtainable under conditions of high fluid shear can be very effective with liquid and multiphase streams as compared to conventional reaction systems. The creation of zones of extreme temperatures and pressures may facilitate non-equilibrium reaction rates. Such local zones, with conditions far different from those of the bulk fluid(s) in a reaction system, are employed to achieve commercially significant production rates for processes that would otherwise be infeasible in conventional industrial processes.

In an embodiment, the organic product is acetaldehyde, but other products of alkanes, olefins, aromatics, or combinations thereof are possible. The high shear device may include a first rotor and a first stator operable together to provide a tip speed of at least about 22.9 m/sec. The tip revolution.

A liquid solvent, such as a Fischer-Tropsch liquid, may be used in the reaction systems described herein. Once a reaction or set of reactions become locally favorable in local zones of high shear, an appropriate catalyst, temperature, and pressure may be created to achieve the desired products. Catalysts, such as hydrogenation or carbonylation catalysts, may be used. The following discussion illustrates how external forces can change the reaction engineering from that predicted by a classical thermodynamic analysis.

Non Equilibrium and External Forces.

External Forces can alter the Classical equilibrium states. Types of external forces include constants like gravity, as well as induced forces such as centrifugal, shear, surface tension, electrostatic, magnetic, electromotive, and acoustical (sonic). Classical chemical thermodynamics neglects external forces except for pressure. Thus, when pressure is the only force, it can be written that:

$$dG=-SdT+v\,dP, \text{ and at constant Pressure and Temperature } dG=0 \quad [\text{Eq. 1}]$$

Therefore, reactions that one would not ordinarily expect to occur based on classical thermodynamics can occur in a high shear system as disclosed.

Potential Reactions of methane and CO and or CO2 [conventionally unfavorable at temperatures of 125° C. to about 725° C.]:

$$CH_4+CO \Leftrightarrow CH_3CHO \text{(acetaldehyde)}$$

$$CH_4+CO \Leftrightarrow H_2C=CO \text{(ketene)}+H2$$

$$CH_4+CO \Leftrightarrow H_2COCH_2 \text{(ethylene oxide)}$$

$$CH_4+CO_2 \Leftrightarrow 2CO+2H_2$$

$$CH_4+CO_2 \Leftrightarrow CH_3COOH \text{(acetic acid)}$$

$$CH_4+CO_2 \Leftrightarrow H_2C=CO \text{(ketene)}+H_2O$$

Potential secondary reactions:

$$CH_4+CH_2O \Leftrightarrow C_2H_4+H2O$$

$$CH_4+CH_2O \Leftrightarrow C_2H_5OH$$

$$CH_4+HCOOH \Leftrightarrow CH_3OH+CH_2O$$

When one looks at the classical method for equilibrium calculations, potential reactions of methane reacting to produce benzene and/or toluene are not favorable, but with high shear the equations change, and the equilibrium may be changed. Example reactions are:

$$CO+5CH4 \rightarrow C6H6+6H2+H2O \qquad \text{Rx. 1.}$$

$$2CO+6CH4 \rightarrow C7H8+5H2+CO2 \qquad \text{Rx. 2.}$$

In an embodiment, the following reactions may take place for ethylene oxide:

$$H2COCH2+RH \rightarrow RCH2CH2OH \text{ (an alcohol)}$$

$$nH_2CHOCH2 \rightarrow OCH2CH2-+-CH2CH2 \\ (OCH2CH2)n\text{-}2 \text{ (a polyethylene oxide chain)}$$

$$H2COCH2+H2 \rightarrow CH3CH2OH \text{ (ethanol)}$$

Classical thermodynamic calculations indicate these reactions are very unfavorable at the conditions of typical Fischer-Tropsch systems but, in accordance with embodiments disclosed herein, an external force can be used to create a favorable equilibrium scenario.

Table 1 shows examples of potential reactions of CH4 and CO that may now be made favorable by the system and method of this disclosure. When Delta $G_0$ is positive the reaction is unfavorable, but where Delta $G_0$ is negative the reaction is favorable. Of particular interest in reactions with CH4 are reactions that result in products containing carbon, hydrogen, and/or oxygen. In some cases the product may contain water or just hydrogen.

TABLE 1

| Reaction Type | | 400K | 600K | 800K | 1000K |
| --- | --- | --- | --- | --- | --- |
| | | $\Delta Gr°$ (kcal/mole of $CH_4$) | | | |
| [10] | $CH_4 + N_2 = HCN + NH_3$ | 36.56 | 35.59 | 34.49 | 33.33 |
| [11] | $CH_4 + \frac{1}{2} O_2 = CO + 2H_2$ | −24.95 | −33.87 | −43.14 | −52.56 |
| [12] | $CH_4 + \frac{1}{2} O_2 = CH_3OH$ | −25.48 | −23.03 | −20.55 | −18.07 |
| [13] | $CH_4 + 2O_2 = C + 2H_2O$ | −96.99 | −96.82 | −96.82 | −96.71 |
| [14] | $CH_4 + 2O_2 = C + 2H_2O_2$ | −35.25 | −29.44 | −23.83 | −18.35 |
| [15] | $2CH_4 + 3/2O_2 = C_2H_2 + 3H_2O$ | −91.87 | −96.64 | −101.70 | −106.76 |
| [16] | $CH_4 + 3/2O_2 = HCOOH + H_2O$ | −125.03 | −122.37 | −119.77 | −117.19 |
| [17] | $CH_4 + O_2 = HCHO + H_2O$ | −69.19 | −70.03 | −70.88 | −71.71 |
| [18] | $CH_4 + O_2 = HCHO + H_2O_2$ | −78.92 | −80.28 | −81.67 | −83.07 |

TABLE 1-continued

| Reaction Type | 400K | 600K | 800K | 1000K |
|---|---|---|---|---|
| | $\Delta Gr°$ (kcal/mole of $CH_4$) | | | |
| Reactions with inorganic compounds | | | | |
| [21] $CH_4 + CO = CH_3CHO$ | 16.05 | 21.90 | 27.70 | 33.43 |
| [22] $CH_4 + CO_2 = 2CO + 2H_2$ | 34.36 | 21.21 | 7.72 | −5.89 |
| [23] $CH_4 + CO_2 = CH_3COOH$ | 19.25 | 24.88 | 30.44 | 35.90 |
| [24] $CH_4 + CO_2 = H_2C = CO + H_2O$ | 36.56 | 34.82 | 32.94 | 31.03 |
| [25] $CH_4 + CO = H_2C = CO + H_2$ | 30.78 | 30.90 | 30.74 | 30.41 |
| [26] $CH_4 + CO = H_2COCH_2$ | 45.74 | 52.71 | 59.64 | 66.48 |
| [37] $CH_4 + H_2O = CO + 3H_2$ | 28.58 | 17.29 | 5.52 | −6.51 |
| [38] $CH_4 + H_2O = CH_3OH + H_2$ | 28.05 | 28.13 | 28.11 | 27.98 |

While preferred embodiments of the disclosure have been shown and described, modifications thereof can be made by one skilled in the art without departing from the spirit and teachings of the disclosure. The embodiments described herein are exemplary only, and are not intended to be limiting. Many variations and modifications of embodiments disclosed herein are possible and are within the scope of the disclosure. Where numerical ranges or limitations are expressly stated, such express ranges or limitations should be understood to include iterative ranges or limitations of like magnitude falling within the expressly stated ranges or limitations (e.g., from about 1 to about 10 includes, 2, 3, 4, etc.; greater than 0.10 includes 0.11, 0.12, 0.13, and so forth). Use of the term "optionally" with respect to any element of a claim is intended to mean that the subject element is required, or alternatively, is not required. Both alternatives are intended to be within the scope of the claim. Use of broader terms such as comprises, includes, having, etc. should be understood to provide support for narrower terms such as consisting of, consisting essentially of, comprised substantially of, and the like.

Accordingly, the scope of protection is not limited by the description set out above but is only limited by the claims which follow, that scope including all equivalents of the subject matter of the claims. Each and every claim is incorporated into the specification as an embodiment of the present disclosure. Thus, the claims are a further description and are an addition to the preferred embodiments of the present disclosure. The disclosures of all patents, patent applications, and publications cited herein are hereby incorporated by reference, to the extent they provide exemplary, procedural or other details supplementary to those set forth herein.

What is claimed is:

1. A method of reacting one or more components in a liquid phase to form an organic product, the method comprising:
   (a) feeding a carbon-based gas and a hydrogen-based liquid medium to a high shear device, the high shear device comprising a shear gap, wherein the carbon-based gas consists of one or more gases selected from the group consisting of carbon dioxide, simple gaseous alkanes, carbon monoxide, and combinations thereof;
   (b) using the high shear device to form a dispersion comprising the carbon-based gas and the hydrogen-based liquid medium, wherein the dispersion comprises gas bubbles with a mean diameter of less than about 1 μm; and
   (c) reacting the dispersion to produce the organic product.

2. The method of claim 1, wherein the high shear device produces a local pressure of at least about 1034.2 MPa (150,000 psi) at the tip of a first rotor disposed therein.

3. The method of claim 2 wherein the organic product comprises alkanes, olefins, aromatics, or combinations thereof.

4. The method of claim 1, wherein the carbon-based gas comprises primarily carbon monoxide and the hydrogen-based liquid medium comprises primarily an alkyl alcohol, an ether, an oxide, water, or a combination thereof.

5. The method of claim 4, wherein the hydrogen-based liquid medium comprises methanol, whereby methanol carbonylation produces organic product comprising acetic acid.

6. The method of claim 5, further comprising feeding hydrogen and at least a portion of the acetic acid organic product to another high shear device, to produce a second organic product comprising ethanol.

7. The method of claim 5, wherein the hydrogen-based liquid medium comprises primarily methanol, dimethyl ether, ethylene oxide, water, or a combination thereof.

8. The method of claim 1 further comprising utilizing a catalyst to promote the formation of the organic product.

9. The method of claim 8, wherein the catalyst comprises a hydrogenation catalyst.

10. The method of claim 9, wherein the catalysts comprises a carbonylation catalyst.

11. The method of claim 1, wherein the high shear device comprises a first rotor and a first stator operable together to provide a tip speed of at least about 22.9 m/sec, wherein the tip speed is defined as $\pi Dn$, where D is the diameter of the first rotor and n is the frequency of revolution.

12. The method of claim 11, wherein the high shear device comprises a second rotor and a second stator proximate to each other and operable together.

13. The method of claim 11, wherein the high shear device produces a localized temperature at a tip of the first rotor of at least 500° C.

14. The method of claim 1, wherein the high shear device produces a localized temperature in the shear gap of at least 125° C.

15. The method of claim 1, wherein the carbon-based gas consists of carbon dioxide, methane, or a combination thereof.

16. A method of reacting a carbon-based component in a methane liquid phase to form an organic product, the method comprising:
   feeding the carbon-based component to a high shear device comprising at least one inlet, at least one outlet, at least one generator configured with a first rotor and a first stator corresponding to the first rotor, wherein the first rotor and the first stator are separated by a shear gap width configured as the minimum distance between the first rotor and the first stator, and wherein the high shear mixing device is capable of producing a tip speed of the first rotor of greater than 22 m/s;
   feeding the methane liquid phase to the high shear device;
   using the high shear device to form a dispersion comprising the carbon-based component and the methane liquid phase, wherein the dispersion comprises gas bubbles with a mean diameter of less than about 5 μm; and
   reacting the dispersion to produce a stream comprising the organic product.

17. The method of claim 16, wherein, wherein the high shear device produces a local pressure of at least about 1034.2 MPa (150,000 psi), and a local temperature of at least about 125° C., at the tip of a first rotor, and wherein at least a portion of the dispersion reacts in the high shear device.

18. The method of claim 17, wherein the carbon-based component comprises carbon monoxide gas.

19. The method of claim 17, wherein the carbon-based component comprises carbon dioxide gas.

20. A method of hydrogenating acetic acid to form an organic product comprising ethanol, the method comprising:

(a) feeding a mixture comprising hydrogen gas and a liquid medium comprising acetic acid to a high shear device, the high shear device comprising a shear gap;
(b) using the high shear device to form a dispersion comprising the hydrogen gas dispersed in the liquid medium, wherein the dispersion comprises hydrogen gas bubbles with a mean diameter of less than about 1 µm; and
(c) reacting the dispersion to produce the organic product comprising ethanol.

* * * * *